US011339178B2

(12) United States Patent
Redinbo et al.

(10) Patent No.: US 11,339,178 B2
(45) Date of Patent: May 24, 2022

(54) INHIBITORS OF MICROBIAL BETA-GLUCURONIDASE ENZYMES AND USES THEREOF

(71) Applicant: The University of North Carolina at Chapel Hill, Chapel Hill, NC (US)

(72) Inventors: Matthew R. Redinbo, Chapel Hill, NC (US); Jian Jin, New York, NY (US); Lindsey James, Chapel Hill, NC (US); Sam Pellock, Chapel Hill, NC (US); Ranathunga Arachchillage Yamuna Ariyarathna, Carrboro, NC (US); Stephen Frye, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/318,991

(22) PCT Filed: Jul. 20, 2017

(86) PCT No.: PCT/US2017/043146
§ 371 (c)(1),
(2) Date: Jan. 18, 2019

(87) PCT Pub. No.: WO2018/017874
PCT Pub. Date: Jan. 25, 2018

(65) Prior Publication Data
US 2019/0330237 A1    Oct. 31, 2019

Related U.S. Application Data

(60) Provisional application No. 62/365,124, filed on Jul. 21, 2016.

(51) Int. Cl.
*C07D 251/00* (2006.01)
*C07D 253/00* (2006.01)
*C07D 495/00* (2006.01)
*C07D 513/14* (2006.01)

(52) U.S. Cl.
CPC ................ *C07D 513/14* (2013.01)

(58) Field of Classification Search
CPC .... C07D 495/14; C07D 513/14; A61K 31/53; A61K 31/5377
USPC .......................................... 544/180; 514/241
See application file for complete search history.

(56) References Cited

U.S. PATENT DOCUMENTS

| | | | |
|---|---|---|---|
| 3,773,919 A | 11/1973 | Boswell et al. | |
| 4,239,887 A | 12/1980 | Youssefyeh et al. | |
| 8,557,808 B2 * | 10/2013 | Redinbo ................ | A61K 31/00 514/232.8 |
| 9,334,288 B2 * | 5/2016 | Redinbo ................ | A61K 31/00 |

| | | | |
|---|---|---|---|
| 2008/0160028 A1 | 7/2008 | Reichelt et al. | |
| 2009/0143399 A1 | 6/2009 | Hurley et al. | |
| 2015/0011542 A1 | 1/2015 | Boelsterli | |

FOREIGN PATENT DOCUMENTS

| | | |
|---|---|---|
| JP | 56-079692 A | 6/1981 |
| WO | WO 2011/072127 A1 | 6/2011 |
| WO | WO 2018/142365 A1 | 8/2018 |

OTHER PUBLICATIONS

Paronikyan et al. Pharmaceutical Chemistry Journal, vol. 40, No. 6, 293-295, 2006.*
Freshney et al.,Culture of Animal Cells, A Manual of Basic Technique, Alan R. Liss, Inc., 1983, New York, p. 4.*
Dermeret al., Bio/Technology, 1994, 12:320.*
Agrawal et al. Current Enzyme Inhibition (2012), 8(1), 22-46; CA 158: 408126, 2012. CAPLUS Abstract provided.*
El-Dean et al. Journal of the Chinese Chemical Society (Taipei, Taiwan) (2008), 55(6), 1290-1299; CA 151: 313483, 2009. CAPLUS Abstract provided.*
European Patent Application No. 17831897.8, Extended European Search Report dated Nov. 29, 2019.
Ahmad et al., "A High Throughput Assay for Discovery of Bacterial Beta-Glucuronidase Inhibitors," Current Chemical Genomics, 5:13-20, (2011).
Boelsterli et al., "Multiple NSAID-Induced Hits Injure the Small Intestine: Underlying Mechanisms and Novel Strategies," Toxicological Sciences, 131(2):654-667, (2013). [Retrieved from the Internet Jan. 28, 2013: <URL: http://toxsci.oxfordjournals.org>].
Doyle et al., "Production and properties of bacterial beta-glucuronidase," J. Biol. Chem., 217(2):921-930, (1955). [Retrieved from the Internet May 15, 2019: <URL: http://www.jbc.org/content/217/2/921.long>].
Farnleitner et al., "Hydrolysis of 4-methylumbelliferyl-beta-D-glucuronide in differing sample fractions of river waters and its implication for the detection of fecal pollution," Water Res., 36(4):975-981, (2002).
Fior et al., "A novel method for fluorometric continuous measurement of β-glucuronidase (GUS) activity using 4-methyl-umbelliferyl-β-d-glucuronide (MUG) as substrate," Plant Sci., 176(1):130-135, (2009).
Hunt et al., "Synthesis and SAR Studies of novel antifungal 1,2,3-triazines," Bioorganic and Medicinal Chemistry Letters, 17(18):5222-5226, (2007).
Kong et al., "Old Drug New Use—Amoxapine and Its Metabolites as Potent Bacterial beta-Glucuronidase Inhibitors for Alleviating Cancer Drug Toxicity," Clin Cancer Res, 20(13):3521-3530, (2014). [Retrieved from the Internet Apr. 26, 2019: <URL: http://clincancerres.aacrjournals.org/content/20/13/3521>].
Loguidice et al., "Pharmacologic Targeting of Bacterial Beta-Glucuronidase Alleviates Nonsteroidal Anti-Inflammatory Drug-Induced Enteropathy in Mice," The Journal of Pharmacology and Experimental Therapeutics, 341(2):447-454, (2012). [Retrieved from the Internet Apr. 16, 2012: <URL: http://jpet.aspetjournals.org>].

(Continued)

*Primary Examiner* — Shobha Kantamneni
(74) *Attorney, Agent, or Firm* — Alston & Bird LLP

(57) ABSTRACT

Compounds and compositions are provided that comprise selective b-glucuronidase inhibitors. The compounds and compositions can ameliorate the side effects of chemotherapeutic agents and can improve the efficacy of such agents, including irinotecan and non-steroidal anti-inflammatory drugs.

3 Claims, 3 Drawing Sheets

(56) References Cited

OTHER PUBLICATIONS

Mani et al., "Understanding and Modulating Mammalian-Microbial Communication for Improved Human Health," Annu. Rev. Pharmacol. Toxicol., 54:559-580, (2014). [Retrieved from the Internet Jan. 8, 2014: <URL: http://www.annualreviews.org>].

Roberts et al., "Molecular Insights into Microbial Beta-Glucuronidase Inhibition to Abrogate CPT-11 Toxicity," Molecular Pharmacology, 84(2):208-217, (2013). [Retrieved from the Internet Jan. 8, 2014: <URL: http:/molpharm.aspetjournals.org>].

Saitta et al., "Bacterial beta-glucuronidase inhibition protects mice against enteropathy induced by indomethacin, ketoprofen or diclofenac: mode of action and pharmacokinetics," Xenobiotica, 44(1):28-35, (2014). [Retrieved from the Internet Jan. 8, 2014: <URL: http://informahealthcare.com>].

Szasz, Gabor, "Comparison between p-nitrophenyl glucuronide and phenolphthalein glucuronide as substrates in the assay of beta-glucuronidase," Clin Chem., 13(9):752-759, (1967). [Retrieved from the Internet May 15, 2019: <URL: http://clinchem.aaccjnls.org/content/clinchem/13/9/752.full.pdf>].

Wallace et al., "Alleviating Cancer Drug Toxicity by Inhibiting a Bacterial Enzyme," Science, 330(6005):831-835, (2010). [Retrieved from the Internet Nov. 4, 2010: <URL: http://www.sciencemag.org>].

Wallace et al., "Structure and Inhibition of Microbiome beta-Glucuronidases Essential to the Alleviation of Cancer Drug Toxicity," Chemistry & Biology, 22(9):1238-1249, (2015).

WIPO Application No. PCT/US2017/043146, PCT International Preliminary Report on Patentability dated Jan. 31, 2019.

WIPO Application No. PCT/US2017/043146, PCT International Search Report and Written Opinion of the International Searching Authority dated Oct. 31, 2017.

Khandwala, Atul et al., "Antiallergic Activity Profile In Vitro of RHC 2963 and Related Compounds," International Journal of Immunopharmacology, 5(6):491-502, (1983).

Khimiya Geterotsiklicheskikh Soedinenii, 1:122-132, (1994).

RN: 847915-26-8, etc., Registry (STN), Apr. 5, 2005.

RN:376371-26-5, all other 7 compounds, Dec. 18, Registry (STN), 2001.

CN Patent Application No. 201780052385.8, Notice of First Office Action dated Apr. 14, 2021.

JP Patent Application No. 2019-502604, Notice of Reasons for Refusal dated Jun. 9, 2021.

\* cited by examiner

INHIBITORS OF MICROBIAL BETA-GLUCURONIDASE ENZYMES AND USES THEREOF

CROSS-REFERENCE TO RELATED APPLICATION(S)

This application is a U.S. National Stage entry of International Application No. PCT/US2017/043146 filed Jul. 20, 2017, which claims the benefit of U.S. Provisional Application No. 62/365,124, filed Jul. 21, 2016, each of which are incorporated herein by reference in their entirety for all purposes.

GOVERNMENT SUPPORT

This invention was made with government support under Grant CA098468 awarded by the National Institutes of Health. The government has certain rights in the invention.

FIELD OF THE INVENTION

The invention relates generally to compounds which are microbial β-glucuronidase ("GUS")-specific inhibitors capable of alleviating the toxicity of certain chemotherapeutic agents, such as anticancer and non-steroidal anti-inflammatory drugs.

BACKGROUND

Irinotecan is a commonly used chemotherapeutic agent used in the treatment of a variety of malignances. Unfortunately, patients treated with Irinotecan often suffer side effects, such as severe diarrhea, which increases patient suffering and thereby reduces the viability for dose escalation and improved efficacy. Currently, no effective therapy exists to overcome such diarrhea. It can be so severe that it, in fact, becomes a dose limiting side effect.

The underlying mechanism of Irinotecan induced diarrhea has been extensively investigated. The mechanism begins with bacteria β-glucuronidase (GUS) enzymes in the intestines converting the nontoxic metabolite of Irinotecan, SN-38G, to toxic SN-38. The compound SN-38 is the therapeutically active form of Irinotecan, which when present in the intestines, leads to damage of intestinal epithelial cells and diarrhea.

The microbial beta-glucuronidase (GUS) enzymes in the mammalian gastrointestinal (GI) tract are the first established drug targets in the microbiome. GUS enzymes have been shown to reactivate drug metabolites to their toxic forms, which can significantly damage the GI epithelium and reduce drug tolerance and efficacy. (Wallace B. D., et al., *Science*, 330, 831-835 (2010)).

Compounds and methods that can safely and effectively prevent the reactivation of drug metabolites are needed. The subject matter described herein addresses this need.

BRIEF SUMMARY

In an embodiment, the subject matter described herein is directed to compounds of Formula I, which are selective microbial GUS inhibitors.

The compounds find use in inhibiting β-glucuronidases from hydrolyzing glucuronides, and thereby attenuate the side effects seen in certain drugs, such as antineoplastic agents. In an embodiment, the subject matter described herein is directed to methods of treating a condition, such as gastrointestinal distress, which often accompanies treatment of diseases, such as cancer, by administering to a subject in need thereof a compound of Formula I or a pharmaceutical formulation thereof.

Another embodiment includes pharmaceutical compositions comprising a compound of Formula I or a pharmaceutically acceptable salt and a pharmaceutically acceptable carrier.

Still another embodiment includes methods of inhibiting β-glucuronidases comprising contacting the β-glucuronidase with an effective amount of a compound of Formula I or a pharmaceutically acceptable salt.

Still another embodiment includes methods of preparing the compounds of Formula I.

Still further embodiments are as described herein.

DETAILED DESCRIPTION

Figure 1:
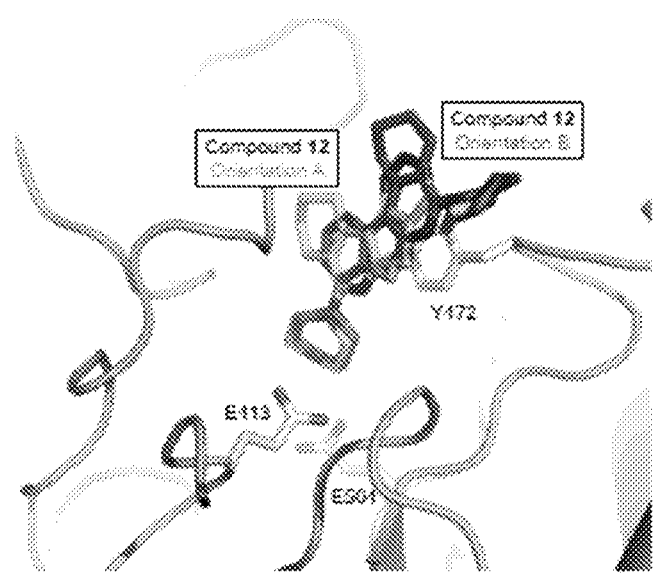
FIG. 1 shows a 2.3 Å resolution crystal structure of EcGUS revealing that the di-piperizine compound 12 binds in two orientations (A and B) at the GUS active site.
Figure 2:
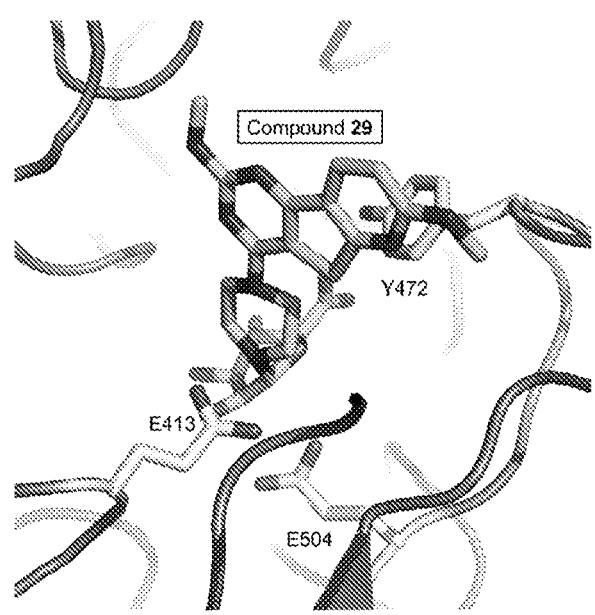
FIG. 2 shows a 2.4 Å resolution crystal structure of a microbial GUS in complex with compound 29 and a glucuronic acid from a substrate molecule co-crystalized with enzyme and compound 29.

The selectively inhibiting agents of Formula I and compositions thereof as disclosed herein can be used in connection with methods for treating cancer and for reducing side effects of antineoplastic agents, such as camptothecin-derived antineoplastic agents. The gastrointestinal distress that typically accompanies treatment with a particular chemotherapeutic agent can be attenuated or ameliorated. The methods are also useful for attenuating or improving any adverse reactions associated with administration of glucuronidase-substrate agent(s) or compound(s). The subject matter described herein includes compositions and methods for inhibiting bacterial β-glucuronidases and for improving efficacy of camptothecin-derived antineoplastic agents or glucuronidase-substrate agents or compounds by attenuating the gastrointestinal distress caused by reactivation of glucuronidated metabolites of such agents.

It has been found that inhibition of microbial beta-glucuronidase (GUS) can alleviate the side effects and toxicity of anticancer drugs, such as irinotecan, as well as several non-steroidal anti-inflammatory drugs. Successful inhibitors of microbial GUS enzymes have the following three characteristics: potency, non-lethality to bacterial and mammalian cells, and selectivity for the microbial GUS enzymes over the mammalian GUS proteins. (Wallace, (2010)). As used herein, "beta-glucuronidase," "β-glucuronidase" and the like means an enzyme (EC 3.2.1.31) capable of hydrolyzing β-glucuronides, but not α-glucuronides or β-glucosides. (Basinska & Florianczyk (2003) *Ann. Univ. Mariae Curie Sklodowska Med.* 58:386-389; Miles et al. (1955) *J. Biol. Chem.* 217:921-930). As used herein, a "glucuronide" and the like means a substance produced by linking glucuronic acid to another substance via a glycosidic bond. Examples of glucuronides of interest herein include, but are not limited to, glucuronides of camptothecin-derived antineoplastic agents such as SN-38G (7-ethyl-10-hydroxycamptothecin glucuronide). Further details of microbiota beta-glucuronidase is disclosed in U.S. Pat. No. 8,557,808, herein incorporated by reference in its entirety.

Reactivation of inactive metabolites such as SN-38G to active SN-38 occurs in the gastrointestinal tract and results from bacterial β-glucuronidases. The reactivated metabolites can lead to a gastrointestinal distress such as diarrhea, which often can be a dose-limiting side effect of the cancer therapy or the therapy to treat any other conditions. As used herein, "dose-limiting" indicates that the side effect from administration of a camptothecin-derived antineoplastic agent or glucuronidase-substrate agents or compounds prevents a subject in need of cancer therapy or therapy to treat any other conditions from receiving a recommended amount. As increasing amounts of the camptothecin-derived antineoplastic agent or glucuronidase-substrate agents or compounds are administered to a subject, increased amounts of glucuronidated metabolites are therefore available as a substrate for the bacterial β-glucuronidases. The resulting reactivated metabolites not only adversely affect a subject's well-being by causing serious side effects, particularly gastrointestinal distress, but also impair treatment outcome by limiting the amount of the camptothecin-derived antineoplastic agent or glucuronidase-substrate agents or compounds that can be administered to the subject.

While not being bound to theory, it is believed that the compounds described herein are inhibitors of hydrolysis of a covalent sugar-enzyme intermediate of the glycosyl hydrolase reaction mechanism. As described herein, the compounds and methods are selective for the bacterial microbiome that re-activates drugs in the gut. Accordingly, the compounds and methods below are useful for ameliorating the side effects of many drugs and treatments.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

The term "substituent" refers to an atom or a group of atoms that replaces a hydrogen atom on a molecule. The term "substituted" denotes that a specified molecule bears one or more substituents. The term "a compound of the formula" or "a compound of formula" or "compounds of the formula" or "compounds of formula" refers to any compound selected from the genus of compounds as defined by Formula I.

As used herein, the term "alkyl" refers to a straight-chained or branched hydrocarbon group. Examples of alkyl groups include methyl, ethyl, n-propyl, isopropyl, tert-butyl, and n-pentyl. Alkyl groups may be optionally substituted with one or more substituents.

The term "benzyl" refers to a hydrocarbon with the formula of $C_6H_5CH_2$ where the point of attachment to the group in question is at the $CH_2$ position. The benzyl may be substituted on the aromatic ring. In one embodiment, 0, 1, 2, 3, 4, or 5 atoms of the aryl group may be substituted by a substituent.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolanyl, tetrahydrofuryl, tetrahydrothienyl, thienyl, and the like.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not minor images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

Furthermore the compounds described herein may include olefins having either geometry: "Z" refers to what is referred to as a "cis" (same side) configuration whereas "E" refers to what is referred to as a "trans" (opposite side) configuration.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

A "metabolite" is a product produced through metabolism in the body of camptothecin-derived antineoplastic agents or glucuronidase-substrate agents or compounds. Metabolites may be identified using routine techniques known in the art and their activities determined using tests such as those described herein. Such products may result, for example, from the oxidation, hydroxylation, reduction, hydrolysis, amidation, deamidation, esterification, deesterification, enzymatic cleavage, and the like, of the administered compound.

The phrase "pharmaceutically acceptable" indicates that the substance or composition must be compatible chemically and/or toxicologically, with the other ingredients comprising a formulation, and/or the subject being treated therewith.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt, the salt can have multiple counter ions. Hence, a pharmaceutically acceptable salt can have one or more charged atoms and/or one or more counter ion. The counter ions may have a positive or negative charge. A positive counter ion may be mono- (e.g. an alkali metal or ammonium), di- (e.g. an earth-alkali metal) or tri-valent (e.g. aluminium). Non-limiting examples of alkali metal cations are $Li^+$, $Na^+$, and $K^+$. Non-limiting examples of negative counter ions include chloride, bromide, iodide, sulfate, alkanesulfonate, arylsulfonate, phosphate, perchlorate, tetrafluoroborate, and nitrate.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Non-limiting examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. In certain embodiments, the pharmaceutically acceptable carrier is a non-naturally occurring pharmaceutically acceptable carrier.

Use of the word "inhibitor" herein is meant to mean a molecule that inhibits activity of microbial GUS enzymes. By "inhibit" herein is meant to decrease the activity of the target enzyme, as compared to the activity of that enzyme in the absence of the inhibitor. In some embodiments, the term "inhibit" means a decrease in GUS activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in GUS activity of about 5% to about 25%, about 25% to about 50%, about 50% to about 75%, or about 75% to 100%. In some embodiments, inhibit means a decrease in GUS activity of about 95% to 100%, e.g., a decrease in activity of 95%, 96%, 97%, 98%, 99%, or 100%. Such decreases can be measured using a variety of techniques that would be recognizable by one of skill in the art, including in vitro assays.

As used herein, a "beta-glucoronidase inhibitor," "GUS inhibitor" or an "inhibitor of GUS" is a compound that reduces, inhibits, or otherwise diminishes one or more of the biological activities of microbial GUS enzyme(s). Inhibition does not necessarily indicate a total elimination of GUS activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of GUS compared to an appropriate control. In some embodiments, the compounds disclosed herein reduce, inhibit, or otherwise diminish microbial GUS enzyme activity.

By "specific inhibition" is intended an agent that reduces, inhibits, or otherwise diminishes the activity of a specific microbial GUS enzyme or ortholog greater than that of another microbial GUS enzyme or ortholog. For example, a specific inhibitor reduces at least one biological activity of a GUS ortholog, e.g., *E. coli* GUS (EcGUS) by an amount that is statistically greater than the inhibitory effect of the compound on another GUS ortholog, e.g., *Streptococcus agalactiae* (SaGUS) or *Clostridium perfringens* (CpGUS). In some embodiments, the IC$_{50}$ of the inhibitor for an ortholog is about 90%, 80%, 70%, 60%, 50%, 40%, 30%, 20%, 10%, 5%, 1%, 0.1%, 0.01%, 0.001% or less of the IC$_{50}$ of the inhibitor for another ortholog. The presently disclosed compounds may or may not be a specific inhibitor. A specific inhibitor reduces the biological activity of a particular GUS by an amount that is statistically greater than the inhibitory effect of the inhibitor on any other GUS.

As used herein, "selectively inhibit" and the like means that a β-glucuronidase inhibitor reduces bacterial, but not mammalian, β-glucuronidase activity. That is, the β-glucuronidase inhibitor can bind to and can prevent bacterial, but not mammalian, β-glucuronidases from hydrolyzing glucuronides. Useful compounds of Formula I are selective for bacterial β-glucuronidase. That is, the compounds decrease activity of the bacterial β-glucuronidase by a statistically significant amount as compared to the mammalian β-glucuronidase. Advantageously, the β-glucuronidase inhibitors described herein are selective for bacterial β-glucuronidases. That is, the compounds inhibit β-glucuronidase in bacteria but do not have inhibitory activity toward mammalian β-glucuronidases, including human β-glucuronidase. While not intending to be bound by any particular mechanism of action, the compounds appear to bind a 12 residue loop in bacterial β-glucuronidases that hovers over an active site opening. The loop is not present in mammalian β-glucuronidases, which therefore can accommodate larger substrates and cleave glucuronic acid moieties from long-chain glycosaminoglycans. The β-glucuronidase inhibitors exhibit other advantages. For example, the compounds do not kill the enteric bacteria or harm human epithelial cells, but are effective against bacteria cultured under aerobic and anaerobic conditions.

As used herein, "enteric bacteria" and the like mean the normal bacteria that inhabit the human gastrointestinal track. Examples of enteric bacteria include, but are not limited to, *Bacteroides* sp. (e.g., *Bacteroides vulgatus*), *Bifidobacterium* sp. (e.g., *Bifidobacterium bifidum* and *Bifidobacterium infantis*), *Catenabacterium* sp., *Clostridium* sp., *Corynebacterium* sp., *Enterococcus* sp. (e.g., *Enterococcus faecalis*), Enterobacteriaceae (e.g., *Escherichia coli*), *Lactobacillus* sp., *Peptostreptococcus* sp., *Propionibacterium* sp., *Proteus* sp., *Mycobacterium* sp., *Pseudomonas* sp. (e.g., *Pseudomonas aeruginosa*), *Staphylococcus* sp. (e.g., *Staphylococcus epidermidis* and *Staphylococcus aureus*) and *Streptococcus* sp. (e.g., *Streptococcus mitis*). Because enteric bacteria commensally inhabit the gastrointestinal tract, they promote gastrointestinal health by preventing infection by opportunistic bacteria like *Clostridium difficle*.

The terms "treat" and "treatment" refer to both therapeutic treatment and prophylactic or preventative measures, wherein the object is to prevent or slow down (lessen) an undesired physiological change or disorder. The terms "alleviate" and "attenuate" refer to the degree and rate of occurrence of the objective and subjective symptomology associated with GI distress. Beneficial or desired clinical results include, but are not limited to, alleviation of symptoms, diminishment of extent of conditions, stabilized (i.e., not worsening) condition, delay or slowing of side effects, lessening of GI distress relative to the GI distress suffered prior to receiving a compound of Formula I. "Treatment" can also mean improved side effects as compared to expected side effects if not receiving treatment. Those in need of treatment include those already with the condition or disorder as well as those prone to have the condition or disorder or those in which the condition or disorder is to be prevented.

The term "administration" or "administering" includes routes of introducing the compound(s) to a subject to perform their intended function.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Additional definitions are also provided below.

II. Compounds

The compounds of Formula I, which also include pharmaceutically acceptable salts, have the following structure:

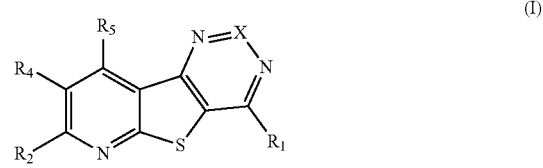

wherein,

R$_1$ is selected from the group consisting of:

i. —OR$_A$, wherein R$_A$ is selected from the group consisting of H, CF$_3$, optionally substituted linear or branched C$_{2-6}$ alkyl, optionally substituted benzyl, and C$_{3-8}$ cycloalkyl;

ii. —NR$_B$R$_C$, wherein R$_B$ and R$_C$ are each independently selected from the group consisting of H, linear or branched C$_{1-6}$ alkyl optionally substituted with amino, optionally substituted benzyl, C$_{2-5}$ heteroaryl, C$_{2-5}$ heteroalkyl, and C$_{3-8}$ cycloalkyl;

iii. C$_{2-5}$ heteroaryl optionally substituted with hydroxyl, halo, or amino;

iv. —N(CH$_2$)$_p$—Z, wherein p is 1 or 2; and Z is heteroaryl or heterocycloalkyl optionally substituted with hydroxyl, halo, or amino;

v.

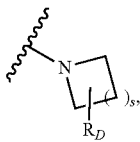

wherein s is 1, 2, or 3; and $R_D$ is amino, hydroxyl, halo, or linear or branched $C_{1-6}$ alkyl; and vi.

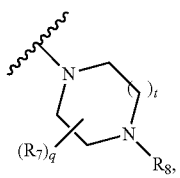

wherein
$R_7$ is H, linear or branched $C_{1-6}$ alkyl optionally substituted with halo, amino, or hydroxyl;
t is 1 or 2;
q is 1 or 2, wherein $R_7$ can form a bridge; and
$R_8$ is H, linear or branched $C_{1-4}$ alkyl optionally substituted with halo, hydroxyl, or amino; or $R_1$ is selected from the group consisting of:
i. —$OR_A$, wherein $R_A$ is selected from the group consisting of H, $CF_3$, optionally substituted linear or branched $C_{2-6}$ alkyl, optionally substituted benzyl, and $C_{3-8}$ cycloalkyl;
ii. —$NR_BR_C$, wherein $R_B$ and $R_C$ are each independently selected from the group consisting of H, linear or branched $C_{1-6}$ alkyl optionally substituted with amino, optionally substituted benzyl, $C_{2-5}$ heteroaryl, $C_{2-5}$ heteroalkyl, and $C_{3-8}$ cycloalkyl;
iii. $C_{2-5}$ heteroaryl optionally substituted with hydroxyl, halo, or amino;
iv. —$N(CH_2)_p$—Z, wherein p is 1 or 2; and Z is heteroaryl or heterocycloalkyl optionally substituted with hydroxyl, halo, or amino;
v.

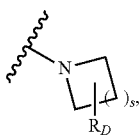

wherein s is 1, 2, or 3; and $R_D$ is amino, hydroxyl, halo, or linear or branched $C_{1-6}$ alkyl;

vi.

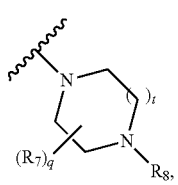

wherein
$R_7$ is H, linear or branched $C_{1-6}$ alkyl optionally substituted with halo, amino, or hydroxyl;
t is 1 or 2;
q is 1 or 2, wherein $R_7$ can form a bridge; and
$R_8$ is H, linear or branched $C_{1-4}$ alkyl optionally substituted with halo, hydroxyl, or amino; and vii.

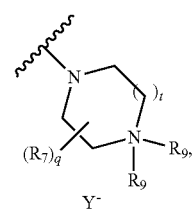

wherein
$R_7$ is H, linear or branched $C_{1-6}$ alkyl optionally substituted with halo, amino, or hydroxyl;
t is 1 or 2;
q is 1 or 2, wherein $R_7$ can form a bridge;
Y is a counterion; and
$R_9$ is, independently in each instance, linear or branched $C_{1-4}$ alkyl optionally substituted with halo, hydroxyl, or amino;

$R_2$ is H, aryl, heterocycloalkyl, or —$NR_FR_G$, wherein
$R_F$ and $R_G$ are independently selected from the group consisting of H, linear or branched $C_{1-6}$ alkyl optionally substituted with halo, amino or hydroxyl, optionally substituted benzyl, and $C_{3-8}$ cycloalkyl;

X is N or —$CR_3$, wherein
$R_3$ is selected from the group consisting of H, halogen, —$OR_I$, and —$NR_IR_J$, wherein
$R_I$ and $R_J$ are each independently selected from H and linear or branched $C_{1-6}$ alkyl, wherein said alkyl can be optionally substituted with hydroxyl; and $R_4$ and $R_5$ are H or are taken together with the carbon to which each is attached to form an optionally substituted $C_{5-7}$ membered ring;

provided that when $R_4$ and $R_5$ taken together form a 6-member unsubstituted ring, X is N or CH, and $R_2$ is morpholinyl, $R_1$ is other than piperazinyl or —$NHCH_2CH_2NH_2$.

In embodiments, $R_4$ and $R_5$ are taken together with the carbon to which each is attached to form an optionally substituted $C_{5-7}$ membered ring.

In any above embodiment, X is N.

In any above embodiment, $R_2$ is heterocycloalkyl.

In any above embodiment, $R_2$ is a 4-8 membered ring containing 1 or 2 nitrogen atoms.

In any above embodiment, $R_2$ is chosen from the group consisting of:

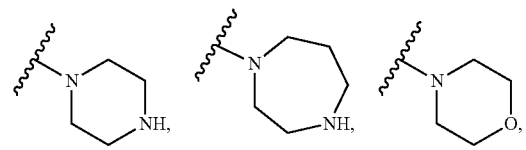

-continued

[chemical structures: piperidinyl, and azetidinyl]

In any above embodiment, R₂ is morpholinyl.
In any above embodiment, R₁ is
—NR_BR_C, wherein R_B and R_C are each independently selected from the group consisting of H, linear or branched $C_{1-6}$ alkyl optionally substituted with amino, optionally substituted benzyl, $C_{2-5}$ heteroaryl, $C_{2-5}$ heteroalkyl, and $C_{3-8}$ cycloalkyl;
R₁ is $C_{2-5}$ heteroaryl optionally substituted with hydroxyl, halo, or amino; or,
R₁ is

[chemical structure with (R₇)_q, ()_t, R₈]

wherein
R₇ is H, linear or branched $C_{1-6}$ alkyl optionally substituted with halo, amino, or hydroxyl;
t is 1 or 2;
q is 1 or 2 and when q is 2 the two R₇ groups may join to form a bridged compound; and
R₈ is H, linear or branched $C_{1-4}$ alkyl optionally substituted with halo, hydroxyl, or amino.

In any above embodiment, R₁ is

[chemical structure with (R₇)_q, ()_t, R₈]

wherein R₇ is H, linear or branched $C_{1-6}$ alkyl optionally substituted with halo, amino, or hydroxyl;
t is 1 or 2;
q is 1 or 2, wherein R₇ can join to form a bridged compound; and
R₈ is H, linear or branched $C_{1-4}$ alkyl optionally substituted with halo, hydroxyl, or amino.

In any above embodiment, t and q are each 1.
In any above embodiment, R₈ is H.
In any above embodiment, R₇ is methyl.
In any above embodiment, R₁ is

[chemical structure with ()_s, R_D]

wherein
s is 1, 2, or 3; and
R_D is amino, hydroxyl, halo, or linear or branched $C_{1-6}$ alkyl; or
R₁ is

[chemical structure with (R₇)_q, ()_t, R₈]

wherein
R₇ is H, linear or branched $C_{1-6}$ alkyl optionally substituted with halo, amino, or hydroxyl;
t is 1 or 2;
q is 1 or 2, wherein R₇ can join to form a bridged compound; and
R₈ is H, linear or branched $C_{1-4}$ alkyl optionally substituted with halo, hydroxyl, or amino.

In any above embodiment, R₁ is particularly

[chemical structure with (R₇)_q, ()_t, R₈]

wherein
R₇ is H, linear or branched $C_{1-6}$ alkyl optionally substituted with halo, amino, or hydroxyl;
t is 1 or 2;
q is 1 or 2, wherein R₇ can join to form a bridged compound; and
R₈ is H, linear or branched $C_{1-4}$ alkyl optionally substituted with halo, hydroxyl, or amino.

In any above embodiment, t and q are each 1.
In any above embodiment, R₇ is H.
In any above embodiment, R₈ is H.
In any above embodiment, R₂ is H, heterocycloalkyl, or —NR_FR_G, wherein
R_F and R_G are independently selected from the group consisting of H, linear or branched $C_{1-6}$ alkyl optionally substituted with halo, amino or hydroxyl, optionally substituted benzyl, and $C_{3-8}$ cycloalkyl.
In any above embodiment, R₂ is heterocycloalkyl.
In a particular embodiment, the compound of Formula I is

[chemical structure of fused polycyclic compound with piperazine groups]

In any above embodiment, $R_2$ is —$NR_FR_G$, wherein
$R_F$ and $R_G$ are independently selected from the group consisting of H, linear or branched $C_{1-6}$ alkyl optionally substituted with halo, amino or hydroxyl, optionally substituted benzyl, and $C_{3-8}$ cycloalkyl.

In any above embodiment, $R_F$ and $R_G$ are independently selected from H or linear or branched $C_{1-6}$ alkyl optionally substituted with halo, amino or hydroxyl.

In a particular embodiment, the compound of Formula I is

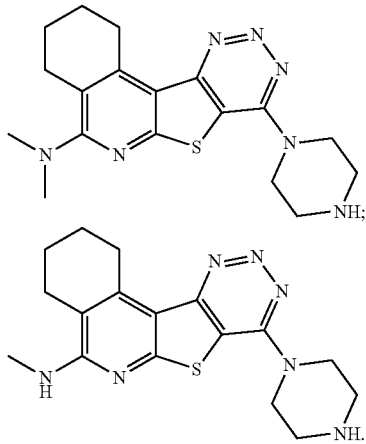

In any above embodiment, wherein $R_4$ and $R_5$ are H.

In any above embodiment, $R_1$ is

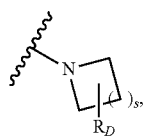

wherein
s is 1, 2, or 3; and
$R_D$ is amino, hydroxyl, halo, or linear or branched $C_{1-6}$ alkyl; or
$R_1$ is

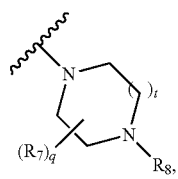

wherein
$R_7$ is H, linear or branched $C_{1-6}$ alkyl optionally substituted with halo, amino, or hydroxyl;
t is 1 or 2;
q is 1 or 2, wherein $R_7$ can join to form a bridged compound; and
$R_8$ is H, linear or branched $C_{1-4}$ alkyl optionally substituted with halo, hydroxyl, or amino.

In any above embodiment, $R_1$ is

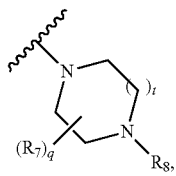

wherein
$R_7$ is H, linear or branched $C_{1-6}$ alkyl optionally substituted with halo, amino, or hydroxyl;
t is 1 or 2;
q is 1 or 2, wherein $R_7$ can join to form a bridged compound; and
$R_8$ is H, linear or branched $C_{1-4}$ alkyl optionally substituted with halo, hydroxyl, or amino.

In any above embodiment, t and q are each 1.

In any above embodiment, $R_7$ is H.

In any above embodiment, $R_1$ is piperazinyl.

In any above embodiment, $R_2$ is H, aryl, heterocycloalkyl, or —$NR_FR_G$, wherein
$R_F$ and $R_G$ are independently selected from the group consisting of H, linear or branched $C_{1-6}$ alkyl, optionally substituted benzyl, and $C_{3-8}$ cycloalkyl.

In any above embodiment, $R_2$ is aryl.

In any above embodiment, $R_2$ is phenyl.

In any above embodiment, $R_2$ is heterocycloalkyl.

In any above embodiment, $R_2$ is a 4-8 membered ring containing 1 or 2 nitrogen atoms contained within the ring.

In any above embodiment, $R_2$ is chosen from the group consisting of:

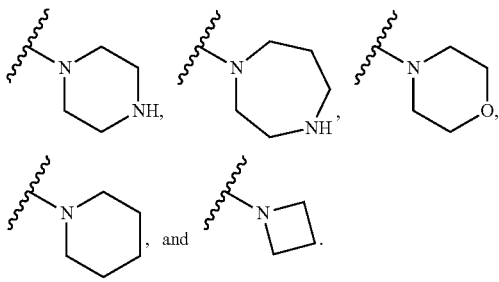

In any above embodiment, $R_2$ is morpholinyl.

In any above embodiment, $R_2$ is —$NR_FR_G$, wherein
$R_F$ and $R_G$ are independently selected from the group consisting of H, linear or branched $C_{1-6}$ alkyl optionally substituted with halo, amino or hydroxyl, optionally substituted benzyl, and $C_{3-8}$ cycloalkyl.

In any above embodiment, $R_F$ and $R_G$ are independently H or linear or branched $C_{1-6}$ alkyl optionally substituted with halo, amino or hydroxyl.

In any above embodiment, $R_F$ and $R_G$ are independently H or unsubstituted linear $C_{1-6}$ alkyl.

In a particular embodiment, the compound of Formula I is or,
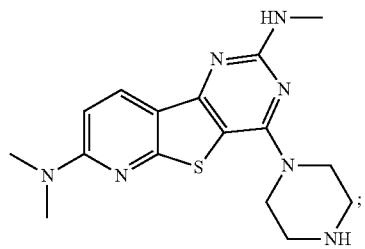
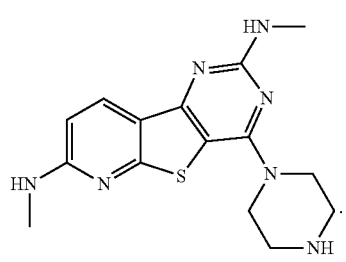
In embodiments, the compound of Formula I is selected from the group consisting of:
2
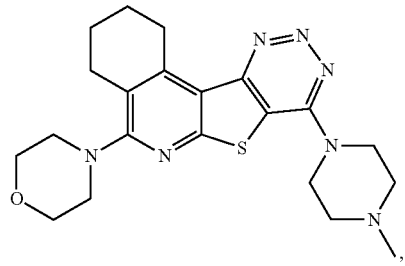
3
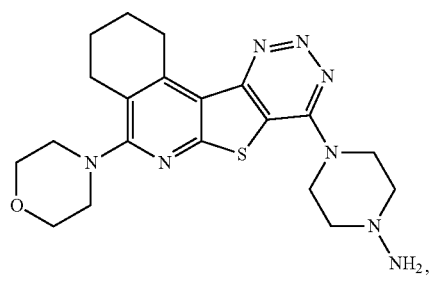
4
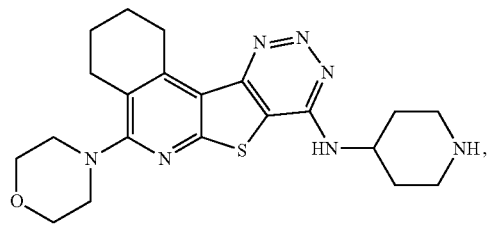
5
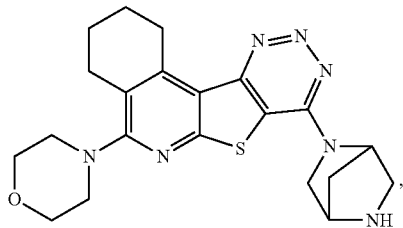
6
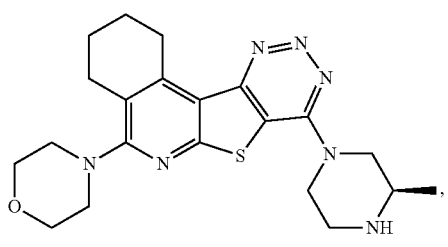
7
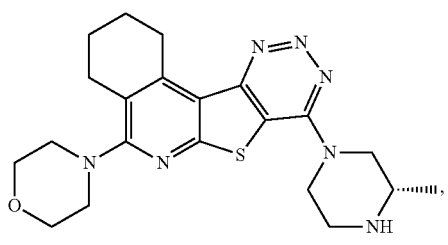
8
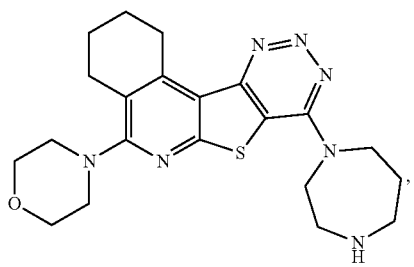
12
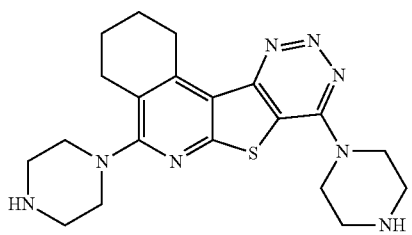
13
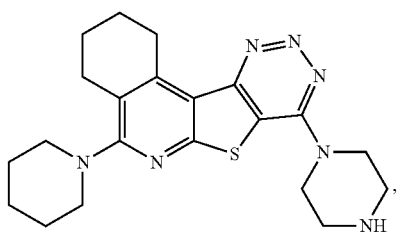

14
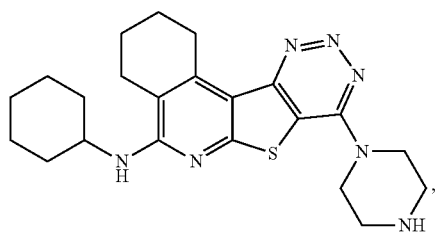
15
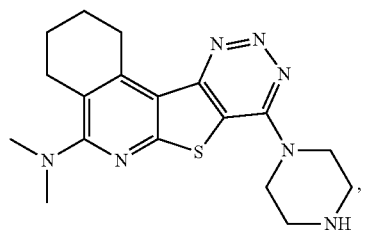
16
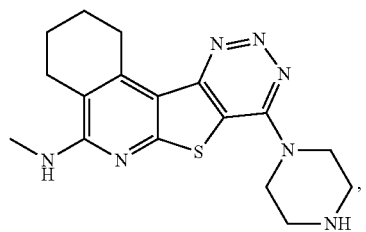
17
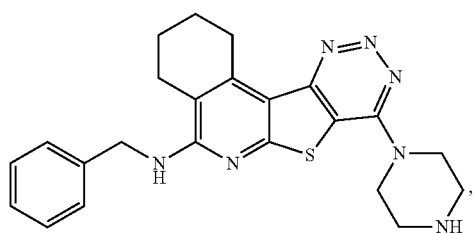
19
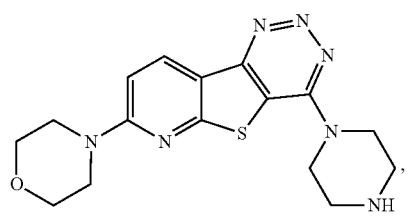
20
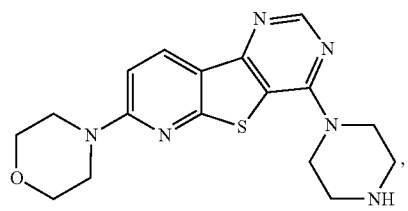
21
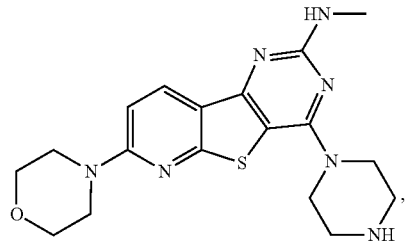
22
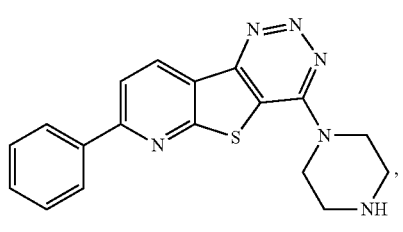
23
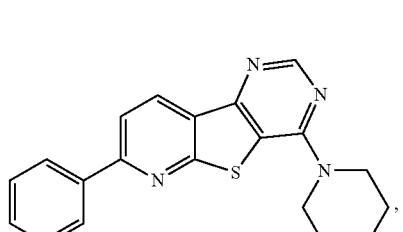
24
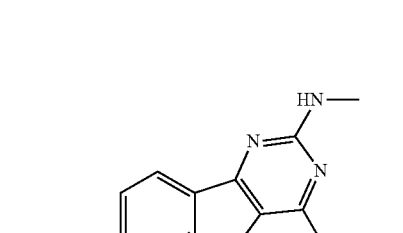
25
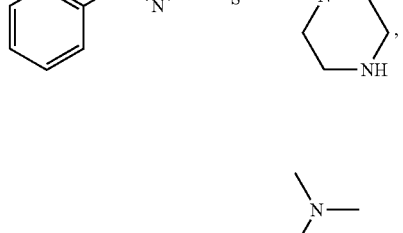
26
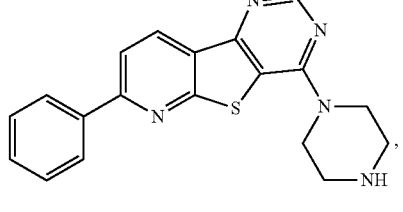
27
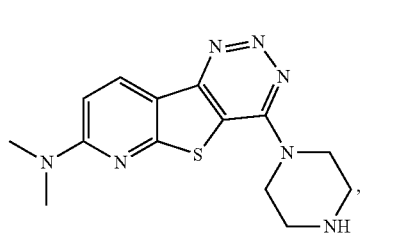

28
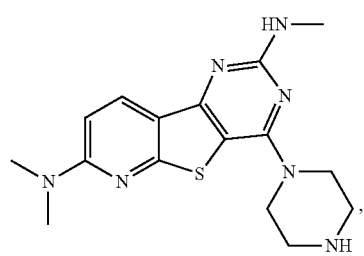
29
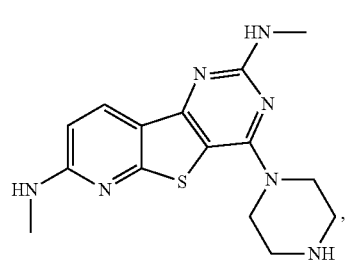
30
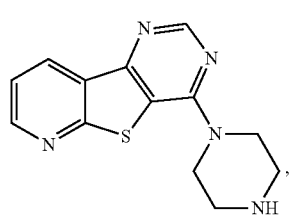
31
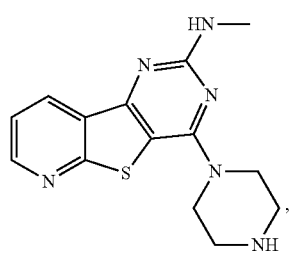
32
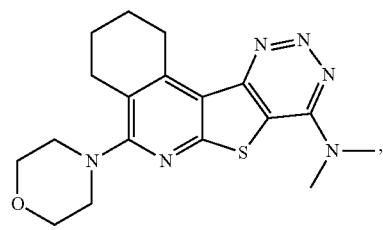
36
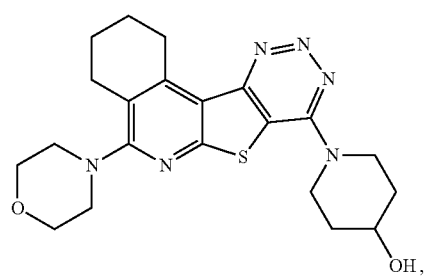
37
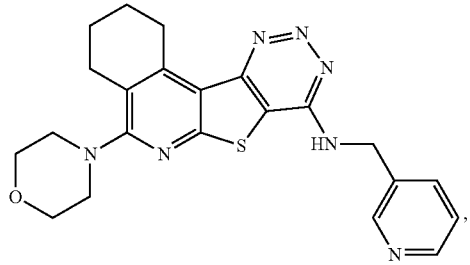
38
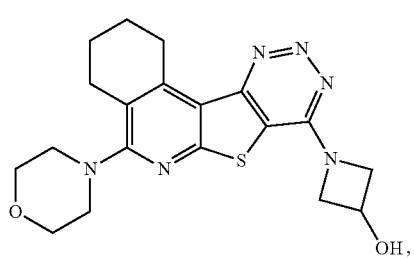
39
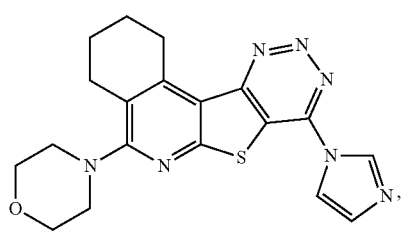
40
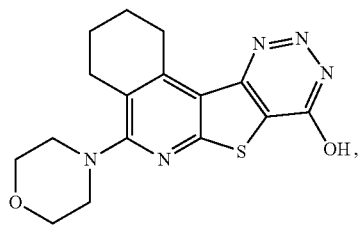
41
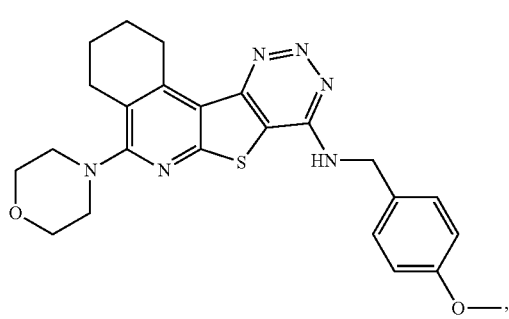

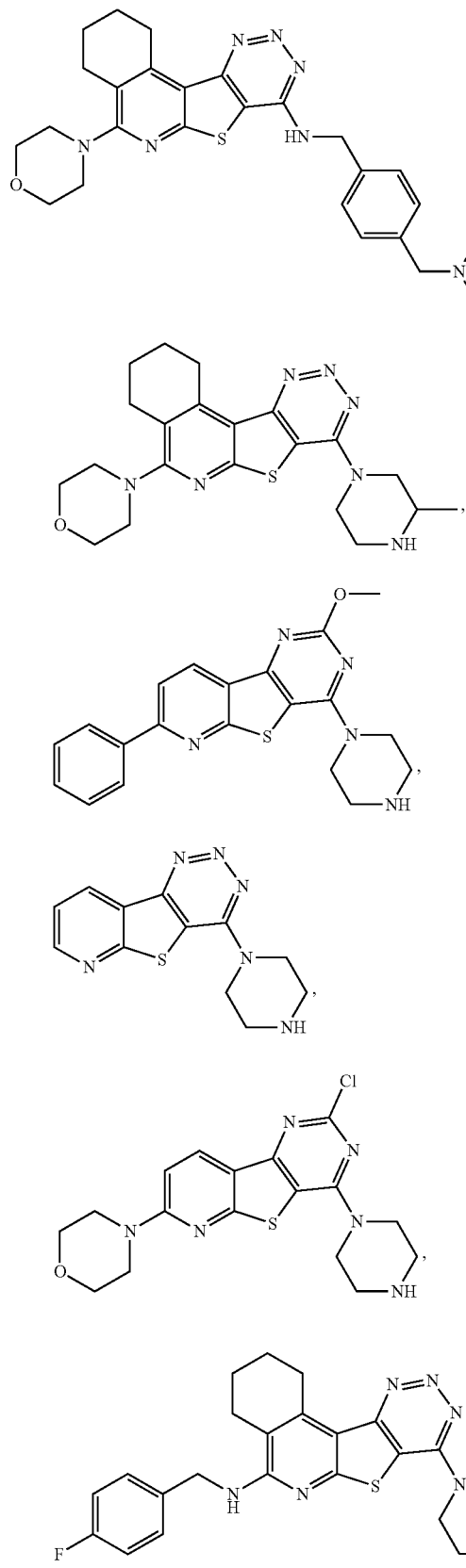
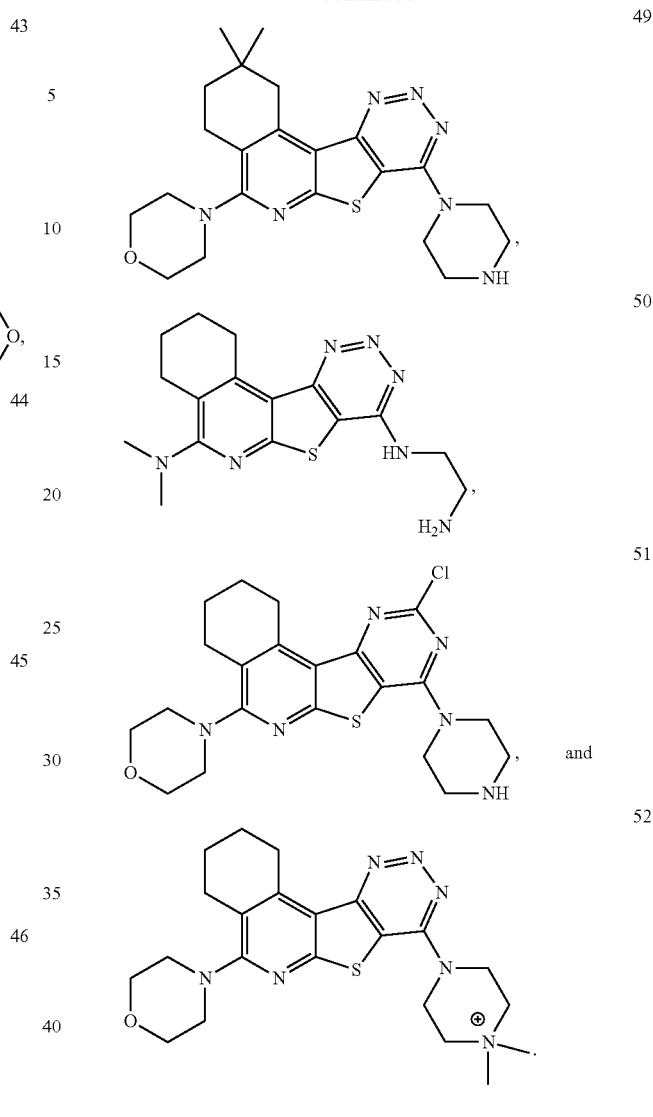

In embodiments, the subject matter described herein is directed to a pharmaceutical composition comprising a compound of Formula I and a pharmaceutically acceptable carrier or excipient.

In embodiments, the subject matter described herein is directed to a method of treating a disease in a subject in need thereof, comprising administering to the subject an effective amount of a compound of Formula I.

The subject matter described herein also includes pharmaceutically acceptable salts of compounds of Formula I.

In any embodiment above, the compound of Formula I specifically inhibits one microbial GUS enzyme or ortholog greater than that of another microbial GUS enzyme or ortholog. In an embodiment, the $IC_{50}$ of the inhibitor for an ortholog is about 90%, 80%, 70%, 60%, 50%, 40%, 30%, 20%, 10%, 5%, 1%, 0.1%, 0.01%, 0.001% or less of the $IC_{50}$ of the inhibitor for another ortholog. In an embodiment, the compound of Formula I specifically inhibits EcGUS in comparison to other GUS orthologs. In an embodiment, the compound of Formula I specifically inhibits SaGUS in comparison to other GUS orthologs. In an embodiment, the compound of Formula I specifically inhibits CpGUS in comparison to other GUS orthologs.

In a further embodiment, the compound of Formula I has an EcGUS $IC_{50}$ in a range from about 1% to about 10% the $IC_{50}$ of any other GUS ortholog. In further embodiments, the compound of Formula I has a EcGUS $IC_{50}$ in a range from about 10% to about 25%, about 25% to about 50%, or about 50% to about 90% the $IC_{50}$ of any other GUS ortholog. In a further embodiment, the compound of Formula I has a SaGUS $IC_{50}$ in a range from about 20% to about 30% the $IC_{50}$ of any other GUS ortholog. In further embodiments, the compound of Formula I has a SaGUS $IC_{50}$ in a range from about 30% to about 50%, about 50% to about 75%, or about 75% to about 90% the $IC_{50}$ of any other GUS ortholog.

If the compound of Formula I is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Illustrative examples of other suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

III. Compositions

Compounds of Formula I can be formulated in accordance with standard pharmaceutical practice as a pharmaceutical composition. According to this aspect, there is provided a pharmaceutical composition comprising a compound of Formula I in association with a pharmaceutically acceptable excipient, such as a carrier or diluent.

A typical formulation is prepared by mixing a Formula I compound and one or more excipients. Suitable excipients are well known to those skilled in the art and include materials such as carbohydrates, waxes, water soluble and/or swellable polymers, hydrophilic or hydrophobic materials, gelatin, oils, solvents, water and the like. The particular excipients used will depend upon the means and purpose for which the compound of Formula I is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of Formula I or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula I or stabilized form of the Formula I compound) (e.g., complex with a cyclodextrin derivative or other known complexation agent) is dissolved in a suitable solvent in the presence of one or more of the excipients described above. The compound of Formula I is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. In one embodiment, the container is a blister pack.

Pharmaceutical formulations may be prepared for various routes and types of administration. For example, a compound of Formula I having the desired degree of purity may optionally be mixed with pharmaceutically acceptable excipients (*Remington's Pharmaceutical Sciences* (1980) $16^{th}$ edition, Osol, A. Ed., Mack Publishing Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compounds of Formula I can be sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions comprising a compound of Formula I can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations. Acceptable excipients are nontoxic to recipients at the dosages and concentrations employed, and may include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride;

phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polysorbates (e.g., TWEEN™), poloxamers (e.g., PLURONICS™) or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences.*

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as injectable microspheres composed of lactic acid-glycolic acid copolymer and leuprolide acetate (LUPRON DEPOT™) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences*. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent.

IV. Methods

The methods described herein provide methods for selectively inhibiting bacterial β-glucuronidases. In the methods, an effective amount of at least one selective β-glucuronidase inhibitor can be administered to a subject in need thereof. That is, a subject being treated with a chemotherapeutic agent, such as a camptothecin-derived antineoplastic agent or glucuronidase-substrate agents or compounds.

Also described herein are methods for improving efficacy of camptothecin-derived antineoplastic agents or glucuronidase-substrate agents or compounds by attenuating reactivation by bacterial β-glucuronidases of glucuronidated metabolites of camptothecin-derived antineoplastic agents or glucuronidase-substrate agents or compounds. In the methods, a therapeutically effective amount of at least one selective β-glucuronidase inhibitor can be administered to a subject having or about to have treatment with a chemotherapeutic agent, particularly a camptothecin-derived antineoplastic agent or any other glucuronidase-substrate agents or compounds.

The compounds disclosed herein can be used in compositions and methods for inhibiting bacterial β-glucuronidases and for improving efficacy of camptothecin-derived antineoplastic agents or glucuronidase-substrate agents or compounds by attenuating the gastrointestinal distress caused by reactivation of glucuronidated metabolites of such agents. The presently disclosed compounds find use in selectively inhibiting the activity of one or more microbial beta-glucuronidase (GUS) enzymes found in the mammalian GI tract. The presently disclosed compounds reduce, inhibit, or otherwise diminish the activity of one or more GUS enzymes. The presently disclosed compounds may or may not be a specific GUS inhibitor. However, the GUS inhibitor is selective for microbial or bacterial beta-glucuronidase as compared to other non-microbial beta-glucuronidases. The methods comprise contacting GUS with an effective amount of a compound of Formula I. Such methods include the following.

The compounds and compositions can be used in methods for treating cancer to reduce the side effects of antineoplastic agents, such as camptothecin-derived antineoplastic agents. Thus, the gastrointestinal distress that typically accompanies treatment with an antineoplastic agent can be attenuated. The methods are also useful for attenuating or improving any adverse reactions associated with administration of glucuronidase-substrate agent(s) or compound(s). Methods of the present invention include administering to a subject in need thereof a therapeutically effective amount of at least one β-glucuronidase inhibiting agent that selectively inhibits bacterial β-glucuronidases from hydrolyzing glucuronides.

A method of ameliorating a side effect in a human in need thereof, comprising administering to said human an effective amount of a compound of Formula I.

A method of inhibiting a GUS comprising, contacting a GUS with a compound of Formula I.

By "contact" is intended bringing the compound within close enough proximity to the target GUS such that the compound is able to inhibit the activity of GUS. The compound can be contacted with GUS in vitro or in vivo via administration of the compound to a subject.

In embodiments, the methods are directed to:

A method for selectively inhibiting bacterial β-glucuronidases, the method comprising administering to a subject in need thereof an effective amount of at least one compound of Formula I. In embodiments, the bacteria are selected from the group consisting of a *Bacteroides* sp., *Bifidobacterium* sp., *Catenabacterium* sp., *Clostridium* sp., *Corynebacterium* sp., *Enterococcus faecalis*, Enterobacteriaceae, *Lactobacillus* sp., *Peptostreptococcus* sp., *Propionibacterium* sp., *Proteus* sp., *Mycobacterium* sp., *Pseudomonas* sp., *Staphylococcus* sp. and *Streptococcus* sp.

A method for improving camptothecin-derived antineoplastic agent efficiency, the method comprising administering to a subject prior to, concurrently with or after administration of a camptothecin-derived antineoplastic agent a therapeutically effective amount of at least one compound of Formula I.

A method for attenuating side effects in a subject being administered a camptothecin-derived antineoplastic agent, the method comprising administering prior to, concurrently with or after administration of a camptothecin-derived antineoplastic agent a therapeutically effective amount of at least one compound of Formula I.

In embodiments, the camptothecin-derived antineoplastic agent is selected from the group consisting of camptothecin, diflomotecan, exatecan, gimatecan, irinotecan, karenitecin, lurtotecan, rubitecan, silatecan and topotecan. In particular, the camptothecin-derived antineoplastic agent is irinotecan.

A method to alleviate gastrointestinal distress associated with chemotherapy comprising: a) administering to an animal an anti-cancer effective amount of a chemotherapeutic agent, and b) administering to the same animal an inhibitory effective amount of a one compound of Formula I. In an aspect of this embodiment, the chemotherapeutic active agent is a camptothecin-derived antineoplastic agent.

A method for improving the efficiency of a glucuronidase-substrate agent or compound, the method comprising administering to a subject prior to, concurrently with or after administration of said agent or compound a therapeutically effective amount of at least one compound of Formula I.

Methods for assessing β-glucuronidase activity are known in the art. See, e.g., Farnleitner et al. (2002) *Water Res.* 36:975-981; Fior et al. (2009) *Plant Sci.* 176:130-135; and Szasz (1967) *Clin. Chem.* 13:752-759. One of skill in the art is familiar with assays for testing the ability of an active compound for selectively inhibiting β-glucuronidases with minor or no toxicity to the bacteria that inhabit the gastrointestinal tract. β-glucuronidase activity of bacteria provided the selective β-glucuronidase inhibitor can be reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% when compared to bacteria not provided the selective β-glucuronidase inhibitor.

In one aspect, provided herein is a method for ameliorating the side effects, in particular the GI side effects, in the treatment of cancer in a subject in need thereof. The term "cancer" refers to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include melanoma, squamous cell cancer (e.g., epithelial squamous cell cancer), lung cancer including melanoma, multiple myeloma, small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, glioblastoma multiforme, KRAS mutant solid tumors, indolent non-Hodgkin's lymphoma, chronic lymphocytic leukemia (CLL), diffuse large B-cell lymphoma, thyroid cancer, non-Hodgkin's lymphoma, basal cell carcinoma, hematological tumors, B-cell non-Hodgkin's lymphoma, acute myeloid leukemia (AML), cervical cancer, ovarian cancer, liver cancer, bladder cancer, hepatoma, breast cancer, including triple negative breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Also included are "hematological malignancies" or "hematological cancer," which are the types of cancer that affect blood, bone marrow, and lymph nodes. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

The presently disclosed compounds may be administered in any suitable manner known in the art. In some embodiments, the compound of Formula I, or a pharmaceutically acceptable salt thereof, is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the compound of Formula I is administered continuously. In other embodiments, the compound of Formula I is administered intermittently. Moreover, treatment of a subject with an effective amount of a compound of Formula I can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of Formula I or a pharmaceutically acceptable salt used for treatment may increase or decrease over the course of a particular treatment. Changes in dosage may result and become apparent from the results of diagnostic assays.

In some embodiments, a compound of Formula I is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg.

In some embodiments, the subject that is administered a compound of Formula I is a mammal, such as domesticated animals (e.g., cows, sheep, cats, dogs, and horses), primates (e.g., humans and non-human primates such as monkeys), rabbits, and rodents (e.g., mice and rats). In some embodiments, the subject treated is a human.

In some embodiments, the methods for ameliorating the side effects or improving the efficacy of a chemotherapeutic drug comprising administering to the subject an effective amount of a compound of Formula I, or a pharmaceutically acceptable salt thereof, further comprises administering the chemotherapeutic drug. For example, a compound of Formula I and a chemotherapeutic agent may be administered sequentially (at different times) or concurrently (at the same time). A compound of Formula I and chemotherapeutic agent may be administered by the same route of administration or by different routes of administration.

The chemotherapeutic agent can be a camptothecin-derived antineoplastic agent. As used herein, "a camptothecin-derived antineoplastic agent" and the like means a cytotoxic quinoline alkaloid that inhibits the DNA enzyme topoisomerase I. Camptothecin-derived antineoplastic agents include, but are not limited to, camptothecin (i.e., (S)-4-ethyl-4-hydroxy-1H-pyrano[3',4':6,7]indolizino[1,2-b]quinoline-3,14-(4H,12H)-dione); diflomotecan (i.e., (5R)-5-ethyl-9,10-difluoro-1,4,5,13-tetrahydro-5-hydroxy-3H,15H-oxepino[3',4':6,7]indolizino[1,2-b]quinoline-3,15-dione); exatecan (i.e., (1S,9S)-1-amino-9-ethyl-5-fluoro-1,2,3,9,12,15-hexahydro-9-hydroxy-4-methyl-10H,13H-benzo(de)pyrano(3',4':6,7)indolizino(1,2-b)quinoline-10,13-dione); gimatecan (i.e., (4S)-11-((E)-((1,1-dimethylethoxy)imino)methyl)-4-ethyl-4-hydroxy-1,12-dihydro-14H-pyrano(3',4':6,7)indolizino(1,2-b)quinoline-3,14(4H)-dion e); irinotecan (i.e., (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate); karenitecin (i.e., (4S)-4-ethyl-4-hydroxy-11-(2-trimethylsilyl)ethyl)-1H-pyrano[3',4':6,7]indolizino[1,2-b]quinoline-3,14(4H,12H)-dione); lurtotecan (i.e., 7-(4-methylpiperazinomethylene)-10,11-ethylenedioxy-20(S)-camptothecin); rubitecan (i.e., (4S)-4-ethyl-4-hydroxy-10-nitro-1H-pyrano[3',4':6,7]indolizino[1,2-b]quinoline-3,14 (4H,12H)-dione); silatecan (i.e., 7-tert-butyldimethylsilyl-10-hydroxycamptothecin); and topotecan (i.e., (S)-10-[(dimethylamino)methyl]-4-ethyl-4,9-dihydroxy-1H-pyrano[3',4':6,7]indolizino[1,2-b]quinoline-3,14(4H,12H)-dione).

Of particular interest is irinotecan (CPT-11 or Camptosan®), which is a potent camptothecin-derived antineoplastic agent for treating solid malignancies of the brain, colon and lung, as well as refractory forms of leukemia and lymphoma. Irinotecan is a prodrug that must be converted into its active form, SN-38 (7-ethyl-10-hydroxy-camptothecin), to have antineoplastic activity. During its excretion, SN-38 is glucuronidated to SN-38 glucuronide (SN-38G) by phase II drug metabolizing UDP-glucurono syltransferases.

The term "glucuronidase-substrate agent(s) or compound(s)" refers to any drug, agent or compound or, in particular, a metabolite thereof that can be a substrate for glucuronidase. Thus, in some instances, a drug, compound or agent that is not itself a substrate, but is metabolized to a substrate is encompassed by the term as used herein. Any drug, compound or agent or metabolite thereof that is glucuronidated, also referred to as glucuronides, can be a substrate for glucuronidase and is also described herein as glucuronidase-substrate agent(s) or compound(s). Many drugs, agents or compounds undergo glucuronidation at some point in their metabolism. Alternatively, the drug, agent or compound may be a glucuronide pro-drug. These glucuronides may have different properties than the parent drug, agent or compound. Glucuronidation can modulate the potency of some drugs: the 6-glucuronide of morphine is a more potent analgesic than the parent compound, whereas the 3-glucuronide is a morphine antagonist. In addition, steroid glucuronidation can produce more active or toxic metabolites under pathophysiological conditions or during steroid therapies.

Drugs, agents or compounds or metabolites thereof which are substrates for glucuronidase can have their respective properties altered by glucuronidase hydrolysis. In a specific, non-limiting example, if the drug, agent, compound or metabolite thereof has been metabolized to a glucuronide, the hydrolysis of the glucuronide can reactivate the drug, agent, compound or metabolite thereof. In many cases, this reactivation can cause adverse reactions. For example, if a glucuronide drug, agent or compound or metabolite thereof is present in the gut, glucuronidase hydrolysis in the gut can lead to gastrointestinal distress.

The methods described herein are useful for attenuating, ameliorating or improving the adverse reactions, such as gastrointestinal distress, caused by the action of glucuronidase on a drug, agent or compound or, in particular, a metabolite thereof. As described fully elsewhere herein, hydrolysis of glucuronides can lead to adverse reactions. The methods described herein inhibit or decrease the activity of β-glucuronidases. The methods can therefore be useful to attenuate, ameliorate or improve adverse reactions, such as gastrointestinal distress, associated with administering such drugs, agents or compounds. The methods can also improve the tolerance of any such drug, agent or compound or metabolite thereof that can form a glucuronide. As such, administration of a glucuronidase inhibitor can rescue or improve a treatment with any drug, agent, or compound, wherein glucuronidase hydrolysis of a glucuronide related to the drug, agent, compound or metabolite thereof is causing one or more adverse reactions, particularly gastrointestinal distress or toxicity. Patient compliance and outlook would also improve with the lessening of adverse reactions.

As mentioned above, the term "glucuronidase-substrate agent(s) or compound(s)" refers to any drug, agent or compound or, in particular, a metabolite thereof that can be a substrate for glucuronidase. These can include any chemical compound useful in the treatment of disease, for example, but not limited to, cancer. Examples of such chemotherapeutic agents include NSAIDs, sorafenib, alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-™1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1 (see, e.g., Nicolaou et al., *Angew. Chem Intl. Ed. Engl.,* 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

V. Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus, according to a further aspect, there is provided a compound library comprising at least 2 compounds, or pharmaceutically acceptable salts thereof.

The General Procedures and Examples provide exemplary methods for preparing Formula I compounds. Those skilled in the art will appreciate that other synthetic routes may be used to synthesize the Formula I compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz or CBZ) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

The following examples are offered by way of illustration and not by way of limitation.

EXAMPLES

Example 1. Synthesis of Inh9 and Compounds 2-8

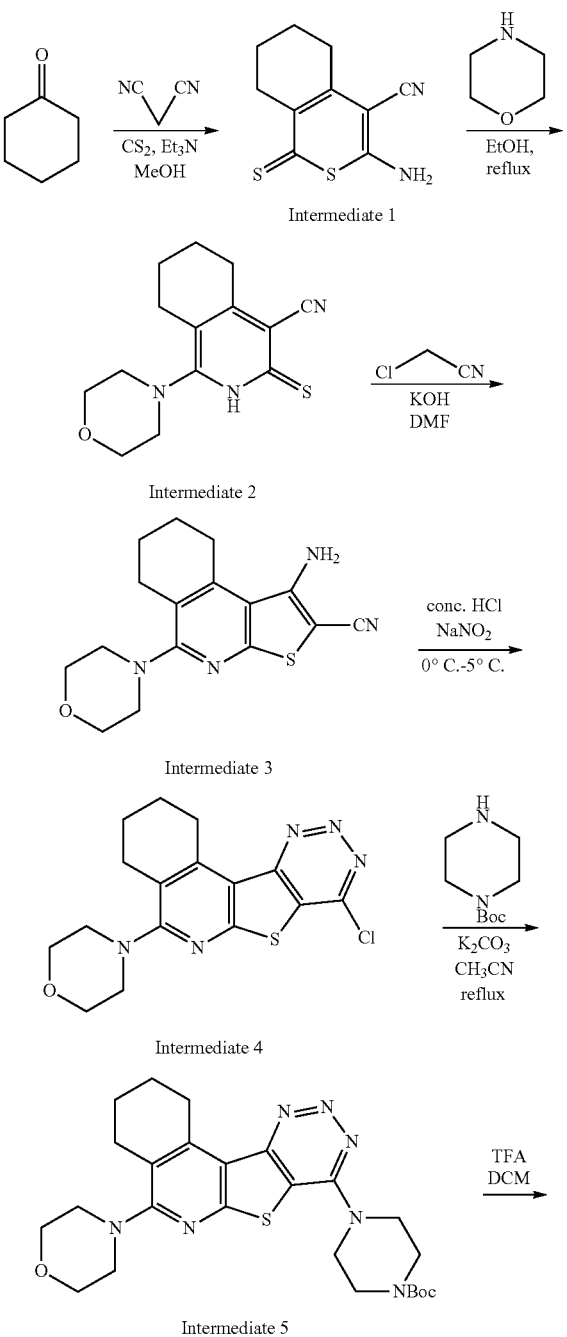

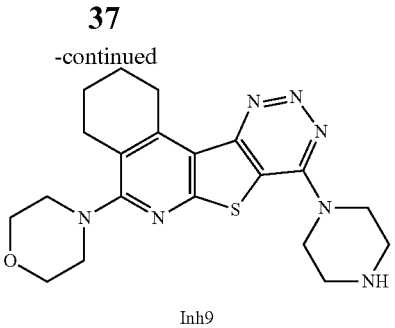

Inh9

Compounds 2-8 in Table 1 were prepared by a similar method as Inh9 from intermediate 4.

Synthesis of Intermediate 1

To a solution of cyclohexanone (5.0 g, 5.3 mL, 51 mmol, 1.0 eq.) in 16 mL of methanol was slowly added carbon disulfide (7.8 g, 6.1 mL, 102 mmol, 2.0 eq.) and malononitrile (3.4 g, 51 mmol, 1.0 eq.), and the mixture was stirred for 5 minutes while maintaining the temperature below 20° C. Triethylamine (2.5 mL) was added, and the reaction mixture was stirred overnight at rt. Precipitated product was filtered, washed with methanol and vacuum dried to provide intermediate 1 as an orange solid (4.3 g, 40%).

$^1$H NMR (400 MHz, DMSO-d$_6$) δ 8.69 (s, 2H), 2.68 (m, 2H), 2.59 (m, 2H), 1.68 (m, 4H)

LC-MS (λ=254 nm): 99%, $t_R$=5.9 min. MS (ESI+): 223 [M+H]$^+$

Synthesis of Intermediate 2

To a suspension of intermediate 1 (4.0 g, 18 mmol, 1.0 eq.) in ethanol (15 mL) was added morpholine (8 mL, 90 mmol, 5 eq.) and the mixture was heated under reflux overnight. Precipitated product was cooled to rt, degassed with nitrogen, filtered, washed with ethanol and vacuum dried to obtain intermediate 2 as an orange solid (3.8 g, 76%).

$^1$H NMR (400 MHz, DMSO-d$_6$) δ 4.33-4.27 (m, 1H), 3.74 (m, 4H), 3.67 (m, 4H), 3.55-3.50 (m, 1H), 2.61 (t, J=5.8 Hz, 2H), 2.41 (t, J=5.8 Hz, 2H), 1.77-1.65 (m, 2H), 1.62-1.52 (m, 2H)

LC-MS (λ=254 nm): 99%, $t_R$=4.9 min. MS (ESI+): 276 [M+H]$^+$

Synthesis of Intermediate 3

To a solution of intermediate 2 (3.0 g, 11 mmol, 1.0 eq.) in 22 mL of DMF was added 2-chloroacetonitrile (0.8 mL, 11.99 mmol, 1.1 eq.) and stirred at rt for an hour. Then the first portion of aq. KOH (10% w/v, 5.5 mL) was added to the reaction mixture and it was stirred at rt overnight, after which a second portion of aq. KOH (10% w/v, 5.5 mL) was added to the reaction mixture and stirred for another 4 hours at rt. Water (50 mL) was added to the precipitated solid product after which it was filtered and vacuum dried to obtain intermediate 3 as a pinkish yellow solid (2.36 g, 69%).

$^1$H NMR (400 MHz, DMSO-d$_6$) δ 6.35 (s, 2H), 3.84-3.70 (m, 4H), 3.27 (t, J=6.5 Hz, 2H), 3.19-3.10 (m, 4H), 2.64 (t, J=5.7 Hz, 2H), 1.88-1.75 (m, 2H), 1.70-1.58 (m, 2H)

LC-MS (λ=254 nm): 99%, $t_R$=5.9 min. MS (ESI+): 315 [M+H]$^+$

Synthesis of Intermediate 4

A solution of sodium nitrite (1.5 g, 22 mmol, 3.0 eq.) in water (7.3 mL) was added dropwise, over 30 minutes to a suspension of intermediate 3 (2.3 g, 7.3 mmol, 1.0 eq.) in conc. HCl acid (15 mL) at 0-5° C. The mixture was stirred for an hour at 0-5° C. and then allowed to stir at rt overnight. Water (100 mL) was added to the precipitated product after which it was filtered, washed with water, and vacuum dried to obtain intermediate 4 as a yellow solid (2.4 g, 92%).

$^1$H NMR (400 MHz, Chloroform-d) δ 3.93-3.85 (m, 2H), 3.75 (t, J=6.6 Hz, 1H), 3.48-3.41 (m, 2H), 2.74 (t, J=5.9 Hz, 1H), 2.08-1.97 (m, 1H), 1.88-1.77 (m, 1H)

LC-MS (λ=254 nm): 99%, $t_R$=6.4 min. MS (ESI+): 362 [M+H]$^+$

Synthesis of Intermediate 5

To a solution of intermediate 4 (85 mg, 0.23 mmol, 1.0 eq.) in CH$_3$CN (2 mL) was added K$_2$CO$_3$ (300 mg) and 1-Boc-piperazine (110 mg, 0.59 mmol, 2.5 eq.) and the reaction mixture was heated under reflux overnight. Upon completion, the reaction was quenched by addition of 20 mL of sat. NaHCO$_3$ solution. The aqueous phase was extracted with CH$_2$Cl$_2$ (3×20 mL) and the organic layers were combined, washed with brine, dried over anhydrous Na$_2$SO$_4$, and filtered. Solvent was removed by rotary evaporation to obtain a dark brown crude material. The crude material was adsorbed onto silica gel and purified by normal phase automated Teledyne Isco chromatography using a CH$_2$C$_{12}$/MeOH/NH$_3$ solvent system. Intermediate 5 was obtained as a pale yellow solid (50 mg, 43%).

$^1$H NMR (400 MHz, Chloroform-d) δ 4.08-4.02 (m, 4H), 3.92-3.83 (m, 4H), 3.77 (t, J=6.7 Hz, 2H), 3.68-3.60 (m, 4H), 3.38-3.30 (m, 4H), 2.73 (t, J=5.8 Hz, 2H), 2.03-1.94 (m, 2H), 1.85-1.76 (m, 2H), 1.49 (s, 9H)

LC-MS (λ=254 nm): 99%, $t_R$=6.5 min. MS (ESI+): 512 [M+H]$^+$

Synthesis of Inh9

To a solution of intermediate 5 (50 mg, 0.098 mmol) in CH$_2$Cl$_2$ (1 mL) at 0° C. was added trifluoroacetic acid (1 mL) and the reaction mixture was stirred until completion at room temperature. The solution was washed with saturated NaHCO$_3$ solution, dried over anhydrous Na$_2$SO$_4$, filtered, and vacuum concentrated to obtain Inh9 as a yellow solid (40 mg, 99%).

$^1$H NMR (400 MHz, Chloroform-d) δ 9.91 (s, 1H), 4.36 (s, 4H), 3.92-3.79 (m, 4H), 3.68 (t, J=6.2 Hz, 2H), 3.48 (s, 3H), 3.40-3.31 (m, 4H), 2.71 (t, J=5.6 Hz, 2H), 1.97 (m, 2H), 1.79 (m, 2H)

LC-MS (λ=254 nm): 99%, $t_R$=5.0 min. MS (ESI+): 412 [M+H]$^+$

Example 2. Synthesis of Compounds 12-17

Scheme 2. Synthesis of compound 15.

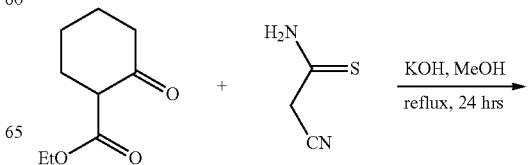

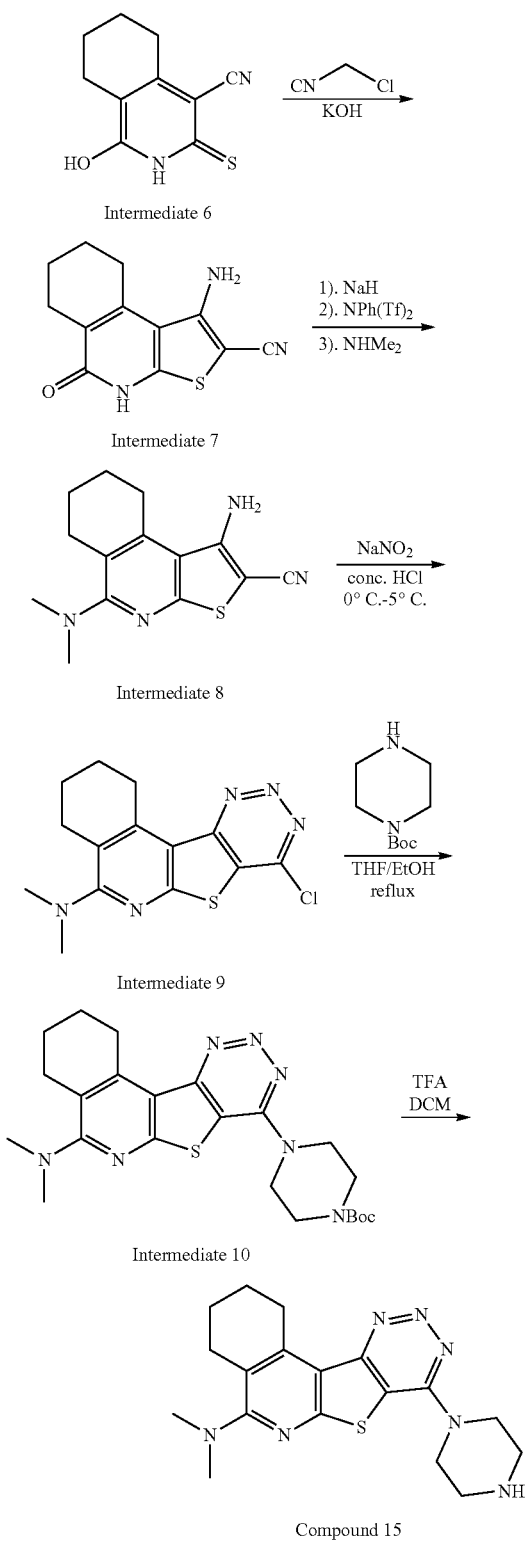

Intermediate 6

Intermediate 7

Intermediate 8

Intermediate 9

Intermediate 10

Compound 15

Intermediates 6 and 7 were synthesized according to the literature (J. C. A. Hunt et al. *Bioorg. Med. Chem. Lett.* 17 (2007) 5222-5226).

Compounds 12-14 and 16-17 in Table 1 were prepared by a similar method as compound 15 from intermediate 7.

Synthesis of Intermediate 8

Intermediate 7 (500 mg, 2.04 mmol, 1.0 eq.) was added portion-wise to a stirred suspension of sodium hydride (60% dispersion in mineral oil, 85 mg, 2.12 mmol, 1.1 eq.) in DMF (10.3 mL) under nitrogen at 0° C. The reaction mixture was stirred at room temperature for 35-40 min. To the resultant solution was added N-phenyl-trifluoromethanesulfonimide (729 mg, 2.04 mmol, 1.0 eq.) in one portion. After 20 min., dimethylamine (1.06 mL, 2.12 mmol, 1.1 eq.) was added to the reaction mixture and stirred overnight. The reaction was slowly quenched with water (5 mL) and extracted with ethyl acetate (3×20 mL). The combined organic fractions were washed with saturated $NaHCO_3$ solution, dried over anhydrous $Na_2SO_4$, filtered, concentrated under reduced pressure, and purified by reverse phase automated Teledyne Isco chromatography using a MeOH/$H_2O$/0.1% acetic acid solvent system. Intermediate 8 was obtained as pale yellow solid (255 mg, 46%).

$^1$H NMR (400 MHz, DMSO-$d_6$) δ 3.22 (t, J=6.5 Hz, 2H), 2.85 (s, 6H), 2.59 (t, J=5.8 Hz, 2H), 1.84-1.72 (m, 2H), 1.60 (m, 2H)

LC-MS (λ=254 nm): 99%, $t_R$=6.1 min. MS (ESI+): 273 [M+H]$^+$

Synthesis of Intermediate 9

A solution of sodium nitrite (266 mg, 3.9 mmol, 3.0 eq.) in water (2 mL) was added dropwise over 30 minutes to a suspension of intermediate 8 (350 mg, 1.3 mmol, 1.0 eq.) in conc. HCl acid (10 mL) at 0-5° C. The mixture was stirred for an hour at 0-5° C. and then allowed to stir at rt overnight. Water (100 mL) was added to the precipitated product after which it was filtered, washed with water, and vacuum dried to obtain intermediate 9 as a pale yellow solid (291 g, 71%).

$^1$H NMR (400 MHz, Chloroform-d) δ 3.68 (t, J=6.6 Hz, 2H), 3.09 (s, 4H), 2.72 (t, J=5.9 Hz, 2H), 2.04-1.93 (m, 2H), 1.81-1.72 (m, 2H)

LC-MS (λ=254 nm): 99%, $t_R$=6.8 min. MS (ESI+): 320 [M+H]$^+$

Synthesis of Intermediate 10

To a solution of intermediate 4 (150 mg, 0.47 mmol, 1.0 eq.) in $CH_3CN$ (4 mL) was added $K_2CO_3$ (300 mg) and 1-Boc-piperazine (219 mg, 1.17 mmol, 2.5 eq.) and the reaction mixture was heated under reflux overnight. Upon completion, the reaction was quenched by addition of 20 mL of sat. $NaHCO_3$ solution. The aqueous phase was extracted with $CH_2Cl_2$ (3×20 mL) and the organic layers were combined, washed with brine, dried over anhydrous $Na_2SO_4$, filtered, and concentrated under reduced pressure to obtain a dark brown crude material. The crude material was adsorbed onto silica gel, and purified by normal phase automated Teledyne Isco chromatography using a $CH_2C_{12}$/MeOH/$NH_3$ solvent system. Intermediate 10 was obtained as a white solid (50 mg, 23%).

$^1$H NMR (400 MHz, Chloroform-d) δ 4.07-3.98 (m, 4H), 3.72 (t, J=6.6 Hz, 2H), 3.62 (dd, J=6.1, 4.3 Hz, 4H), 3.01 (s, 6H), 2.71 (t, J=5.9 Hz, 2H), 2.01-1.89 (m, 2H), 1.76 (m, 2H), 1.48 (s, 9H)

LC-MS (λ=254 nm): 99%, $t_R$=6.9 min. MS (ESI+): 470 [M+H]$^+$

Synthesis of Compound 15

To a solution of intermediate 10 (50 mg, 0.106 mmol) in $CH_2Cl_2$ (1 mL) at 0° C. was added trifluoroacetic acid (1 mL), and the reaction mixture was stirred until completion at room temperature. The solution was washed with saturated NaHCO$_3$ solution, dried over anhydrous Na$_2$SO$_4$, filtered, and vacuum concentrated to obtain compound 15 as a white solid (35 mg, 90%).

$^1$H NMR (400 MHz, DMSO-d$_6$) δ 4.15-4.06 (m, 4H), 3.59 (t, J=6.5 Hz, 2H), 3.29-3.21 (m, 4H), 3.00 (s, 6H), 2.73 (t, J=5.8 Hz, 2H), 1.98-1.87 (m, 2H), 1.77-1.64 (m, 2H)

LC-MS (λ=254 nm): 99%, t$_R$=5.6 min. MS (ESI+): 370 [M+H]$^+$

Example 3. Synthesis of Compound 18

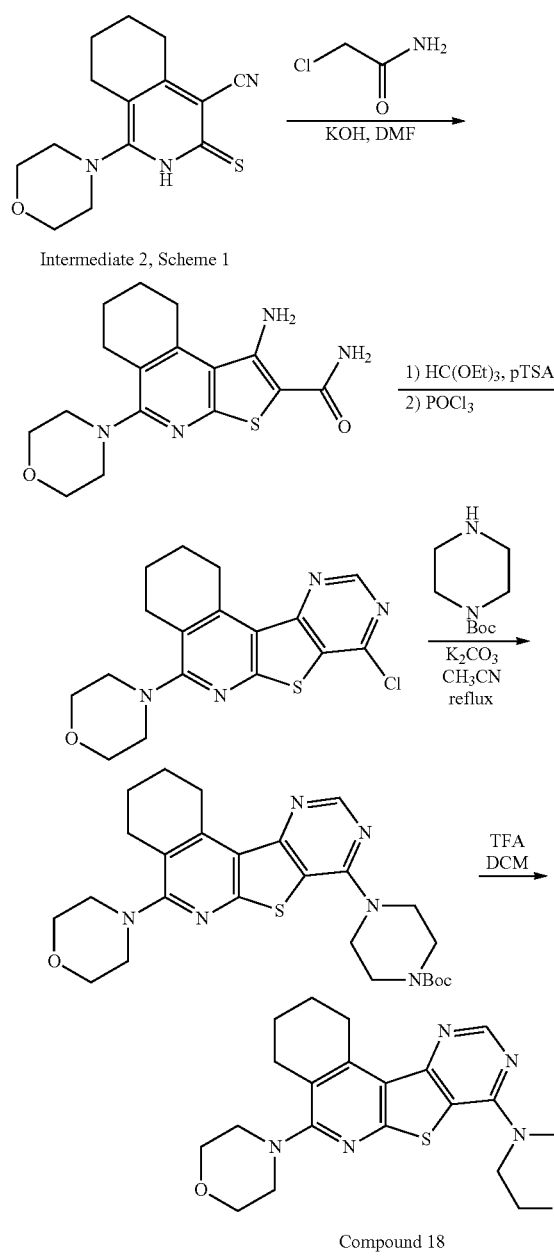

Example 4. Synthesis of Compounds 21, 28 and 29

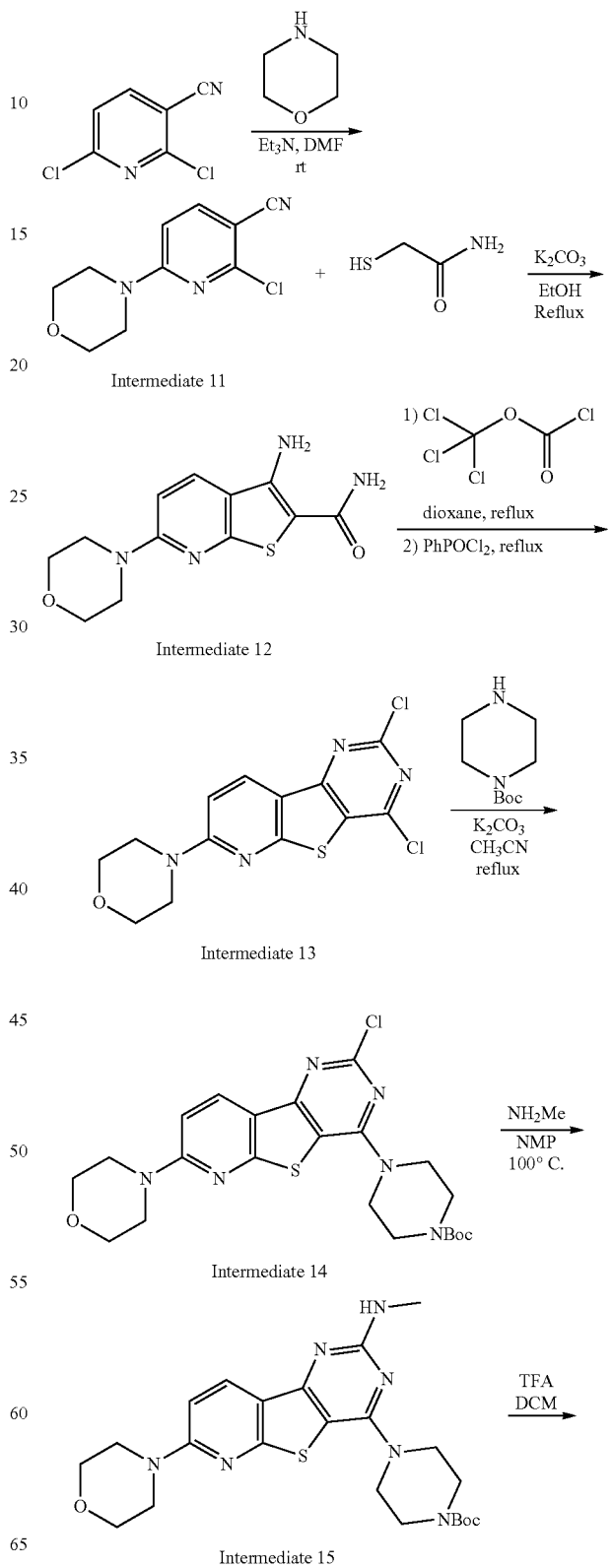

-continued

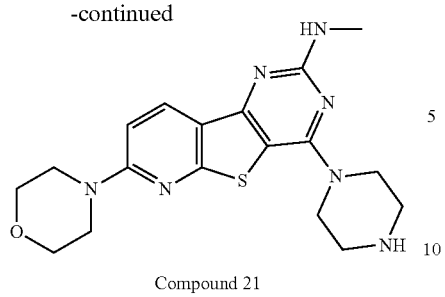

Compound 21

Compounds 28 and 29 in Table were prepared by a similar method as compound 21.

Synthesis of Intermediate 11

2,6-Dichloropyrdiatne-3-carbonitrile (300 g, 1.73 mmol, 1.0 eq.) was dissolved in DMF (2 mL) in a flame dried round bottom flask under nitrogen atmosphere. To the resultant solution was added morpholine (0.15 me, 1.73 mmol, 1.0 eq.), and triethylamine (0.5 mL, 3.46 mmol, 2.0 eq.). The reaction was stirred overnight at room temperature under nitrogen. The reaction was quenched with saturated aqueous $NH_4C$ solution (10 mL). The aqueous phase was separated and extracted with EtOAc (5×10 mL). All combined organic layers were dried over anhydrous $Na_2SO_4$, filtered, and concentrated under reduced pressure to obtain a white crude material. $^1$H NMR and LC-MS of the crude material showed the presence both mono- and di-amination products (6:1, same $t_R$). The crude material was used in the next reaction without further purification (350 mg).

Synthesis of Intermediate 12

Crude intermediate 11 (350 mg) was dissolved in ethanol (9 mL) in a flame dried round bottom flask under an atmosphere of nitrogen. To the resultant solution was added 2-mercaptoacetamide (100 mg/1 mL in methanolic ammonia solution, 1.71 mL, 1.88 mmol) and anhydrous $K_2CO_3$ (521 mg, 3.8 mmol). The reaction was refluxed overnight at 100° C. under nitrogen. The reaction was quenched with water (50 mL) which precipitated the desired product. The precipitated product was filtered, washed with water (50 mL), and concentrated under reduced pressure to obtain intermediate 12 as a pale yellow solid (299 mg, 68% over two steps).

$^1$H NMR (400 MHz, DMSO-$d_6$) δ 8.11 (d, J=9.1 Hz, 1H), 7.03 (brs, 2H), 6.93 (d, J=9.1 Hz, 1H), 6.82 (brs, 2H), 3.73-3.67 (m, 4H), 3.59-3.53 (m, 4H)

LC-MS (λ=254 nm): 99%, $t_R$=4.6 min. MS (ESI+): 279 [M+H]$^+$

Synthesis of Intermediate 13

Intermediate 12 (150 mg, 1.56 mmol, 1.0 eq.) was dissolved in dioxane (2 mL) in a flame dried round bottom flask under nitrogen atmosphere. To the resultant solution was added trichloromethyl chloroformate (0.07 mL, 0.61 mmol, 1.1 eq.), and the reaction was refluxed for 3 hours at 102° C. under nitrogen. The reaction was slowly quenched with water (10 mL). The precipitated product was filtered, washed with water (50 mL), and concentrated under reduced pressure to obtain a yellow solid (118 mg, 69%).

$^1$H NMR (400 MHz, DMSO-$d_6$) δ 12.03 (brs, 1H), 11.29 (brs, 1H), 8.33 (d, J=9.3 Hz, 1H), 7.10 (d, J=9.3 Hz, 1H), 3.70 (m, 4H), 3.68-3.60 (m, 4H)

LC-MS (λ=254 nm): 99%, $t_R$=5.0 min. MS (ESI+): 305 [M+H]$^+$

The above yellow solid (110 mg, 0.36 mmol, 1.0 eq.) was added to phenylphosphonic dichloride (4 mL) in a flame dried round bottom flask under nitrogen atmosphere. The reaction was refluxed for 2 hours at 170° C. under nitrogen. The reaction was slowly quenched with water (10 mL) which precipitated the desired product. The precipitated product was filtered, washed with more water (30 mL), and concentrated under reduced pressure to obtain intermediate 13 as a yellow solid (>30 mg, >25%).

$^1$H NMR (400 MHz, Chloroform-d) δ 8.34 (d, J=9.1 Hz, 1H), 6.80 (d, J=9.1 Hz, 1H), 3.85-3.75 (m, 8H)

LC-MS (λ=254 nm): 99%, $t_R$=5.6 min. MS (ESI+): 342 [M+H]$^+$

Synthesis of Intermediate 14

To a solution of intermediate 13 (90 mg, 0.088 mmol, 1.0 eq.) in $CH_3CN$ (2 mL) was added $K_2CO_3$ (300 mg) and 1-Boc-piperazine (82 mg, 0.43 mmol, 5.0 eq.), and the reaction mixture was heated under reflux overnight. Upon completion, the reaction was quenched by addition of 20 mL of sat. $NaHCO_3$ solution. The aqueous phase was extracted with $CH_2Cl_2$ (3×20 mL) and the organic layers were combined, washed with brine, dried over anhydrous $Na_2SO_4$, filtered, and concentrated under reduced pressure to obtain a dark brown crude material. The crude material was adsorbed onto silica gel and purified by normal phase automated Teledyne Isco chromatography using a $CH_2C_{12}$/MeOH/$NH_3$ solvent system. Intermediate 14 was obtained as a pale yellow solid (40 mg, 93%).

$^1$H NMR (400 MHz, Chloroform-d) δ 8.31 (d, J=9.0 Hz, 1H), 6.76 (d, J=9.1 Hz, 1H), 3.97-3.90 (m, 4H), 3.85-3.77 (m, 4H), 3.73-3.65 (m, 4H), 3.58 (m, 4H), 1.47 (s, 9H)

LC-MS (λ=254 nm): 99%, $t_R$=6.6 min. MS (ESI+): 492 [M+H]$^+$

Synthesis of Intermediate 15

Intermediate 14 (110 mg, 0.36 mmol, 1.0 eq.) was added to methylamine (2M in THF, 5 mL) in a flame dried sealed tube under nitrogen atmosphere. The reaction was heated for 5 days at 100° C. The reaction was then quenched with water (15 mL) and extracted with ethyl acetate (3×20 mL). The combined organic fractions were washed with sat. $NaHCO_3$ solution, dried over anhydrous $Na_2SO_4$, filtered, concentrated under reduced pressure, and purified by reverse phase automated Teledyne Isco chromatography using MeOH/$H_2O$/0.1% acetic acid solvent system. Intermediate 15 was obtained as an orange solid (74 mg, 54%).

$^1$H NMR (400 MHz, Chloroform-d) δ 9.50 (brs, 1H), 8.61 (d, J=8.4 Hz, 1H), 6.82 (d, J=9.3 Hz, 1H), 4.05 (dd, J=6.1, 4.3 Hz, 4H), 3.83-3.78 (m, 4H), 3.73-3.69 (m, 4H), 3.65-3.60 (m, 4H), 2.99 (d, J=3.5 Hz, 3H), 1.23 (s, 9H)

LC-MS (λ=254 nm): 99%, $t_R$=5.6 min. MS (ESI+): 487 [M+H]$^+$

Synthesis of Compound 21

To a solution of intermediate 15 (30 mg, 0.06 mmol) in $CH_2Cl_2$ (2 mL) at 0° C. was added trifluoroacetic acid (2 mL), and the reaction mixture was stirred until completion at room temperature. The solution was washed with saturated $NaHCO_3$ solution, dried over anhydrous $Na_2SO_4$, filtered, and vacuum concentrated to obtain compound 21 as a white solid (10 mg, 10%).

¹H NMR (400 MHz, DMSO-d₆) δ 8.93 (brs, 1H), 8.23 (d, J=9.1 Hz, 1H), 7.08 (d, J=9.1 Hz, 1H), 4.02 (s, 4H), 3.68 (m, 8H), 3.29 (s, 4H), 2.89 (s, 3H)

LC-MS (λ=254 nm): 99%, $t_R$=4.2 min. MS (ESI+): 387 [M+H]⁺

Example 5. Synthesis of Compound 20

Scheme 5. Synthesis of compound 20.

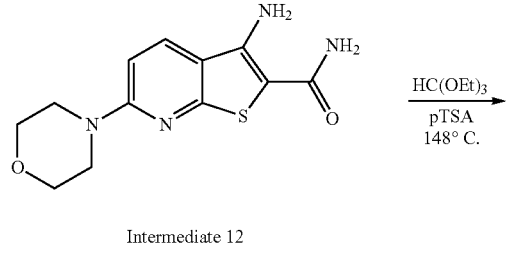

Intermediate 12

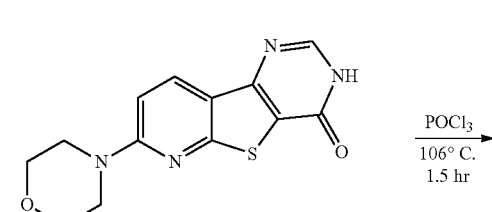

Intermediate 16

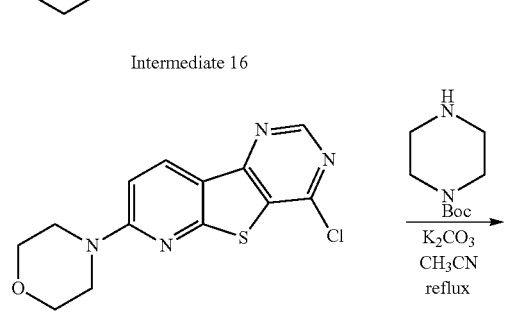

Intermediate 17

Intermediate 18

Compound 20

Example 6. Synthesis of Compound 19

Scheme 6. Synthesis of compound 19.

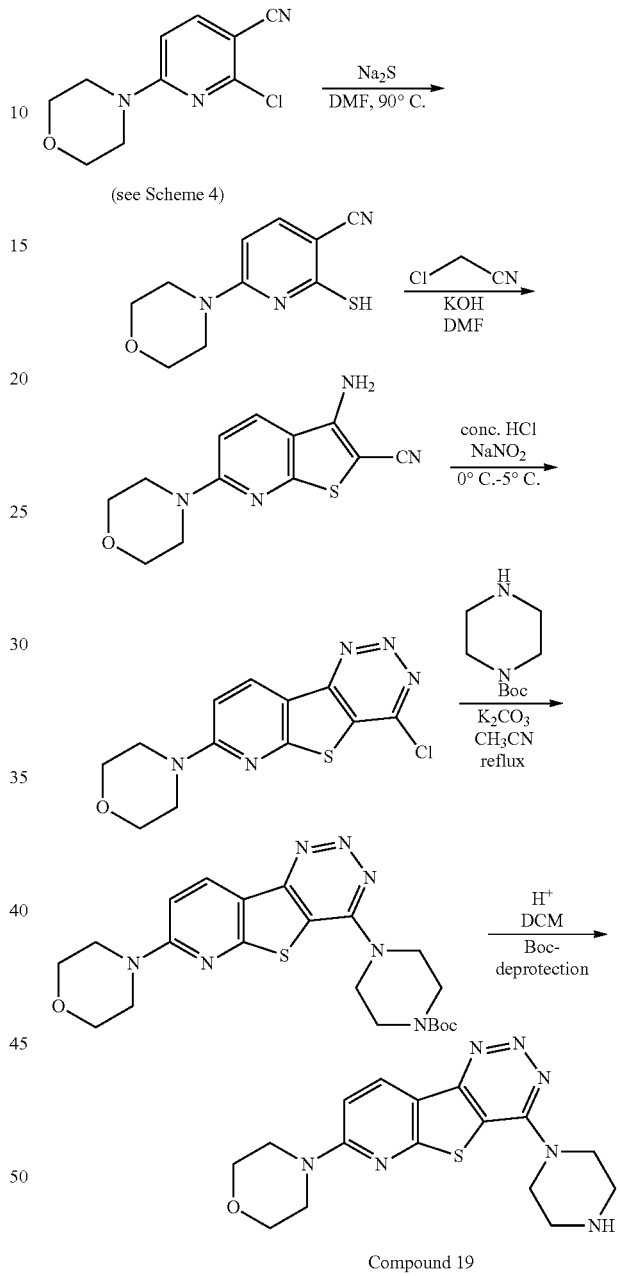

Compound 19

Compound 27 in Table 1 was prepared by a similar method as compound 19.

Synthesis of Intermediate 16

Intermediate 12 (150 mg, 0.54 mmol, 1.0 eq.) was added to triethyl orthoformate (5 mL, excess) followed by p-toluenesulfonic acid monohydrate (10.2 mg, 0.05 mmol, 0.1 eq.) in a flame dried round bottom flask under nitrogen atmosphere. The reaction was refluxed overnight at 148° C. under nitrogen. The reaction was quenched with water (15 mL) and extracted with ethyl acetate (3×20 mL). The combined organic fractions were washed with saturated NaHCO₃ solution, dried over anhydrous Na₂SO₄, filtered, and concentrated under reduced pressure to obtain a yellow product which was used in the next reaction without further purification (155 mg, quantitative).

¹H NMR (400 MHz, DMSO-d₆) δ 8.25 (s, 1H), 8.22 (d, J=9.1 Hz, 1H), 7.12 (d, J=9.1 Hz, 1H), 3.69 (m, 8H)

LC-MS (λ=254 nm): 99%, t_R=5.1 min. MS (ESI+): 289 [M+H]⁺

Synthesis of Intermediate 17

Intermediate 16 (150 mg, 0.52 mmol, 1.0 eq.) was added to phosphoryl chloride (3 mL, excess) in a flame dried round bottom flask under nitrogen atmosphere. The reaction was refluxed for 90 minutes at 106° C. The reaction was cooled and concentrated under reduced pressure to obtain a dark black crude material. This crude material was used in the next reaction without further purification (158 mg, quantitative).

¹H NMR (400 MHz, Chloroform-d) δ 8.95 (s, 1H), 8.47 (d, J=9.1 Hz, 1H), 6.85 (d, J=9.1 Hz, 1H), 3.88-3.79 (m, 8H)

LC-MS (λ=254 nm): 99%, t_R=6.1 min. MS (ESI+): 308 [M+H]⁺

Synthesis of Intermediate 18

To a solution of intermediate 17 (150 mg, 0.5 mmol, 1.0 eq.) in CH₃CN (7 mL) was added K₂CO₃ (300 mg) and 1-Boc-piperazine (455 mg, 2.4 mmol, 5.0 eq.) and the reaction mixture was heated under reflux overnight. Upon completion, the reaction was quenched by addition of 20 mL of sat. NaHCO₃ solution. The aqueous phase was extracted with CH₂Cl₂ (3×20 mL) and the organic layers were combined, washed with brine, dried over anhydrous Na₂SO₄, filtered, and concentrated under reduced pressure to obtain a dark brown crude material. The crude material was adsorbed onto silica gel and purified by normal phase automated Teledyne Isco chromatography using a CH₂Cl₂/MeOH/NH₃ solvent system. Intermediate 18 was obtained as a yellow solid (39 mg, 17%).

¹H NMR (400 MHz, Chloroform-d) δ 8.61 (s, 1H), 8.32 (d, J=9.0 Hz, 1H), 6.77 (d, J=9.0 Hz, 1H), 3.95-3.88 (m, 4H), 3.84-3.66 (m, 8H), 3.61-3.54 (m, 4H), 1.47 (s, 9H)

LC-MS (λ=254 nm): 99%, t_R=6.3 min. MS (ESI+): 457 [M+H]⁺

Synthesis of Compound 20

To a solution of intermediate 18 (39 mg, 0.08 mmol) in CH₂Cl₂ (2 mL) at 0° C. was added trifluoroacetic acid (2 mL) and the reaction mixture was stirred until completion at room temperature. The solution was washed with saturated NaHCO₃ solution, dried over anhydrous Na₂SO₄, filtered, and vacuum concentrated to obtain compound 20 as a pale yellow solid (29 mg, 99%).

¹H NMR (400 MHz, DMSO-d₆) δ 8.92 (brs, 1H), 8.67 (s, 1H), 8.34 (d, J=9.1 Hz, 1H), 7.14 (d, J=9.1 Hz, 1H), 4.11-4.05 (m, 4H), 3.75-3.67 (m, 8H), 3.30 (s, 4H)

LC-MS (λ=254 nm): 99%, t_R=6.6 min. MS (ESI+): 357 [M+H]⁺

Example 7. Synthesis of Compound 22

Scheme 7. Synthesis of compound 22.

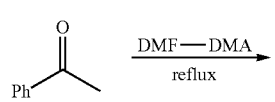

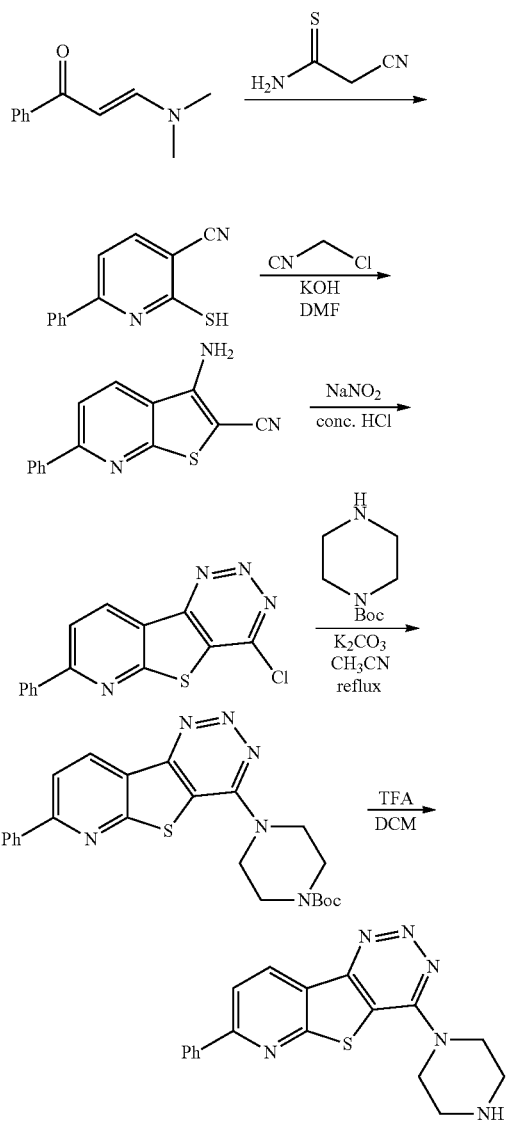

Compound 22

Example 8. Synthesis of Compounds 24-26

Scheme 8. Synthesis of compound 25.

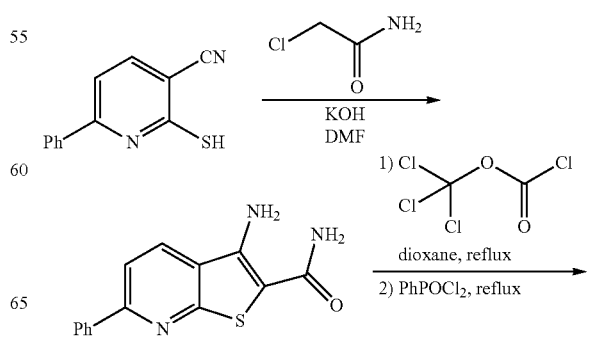

-continued
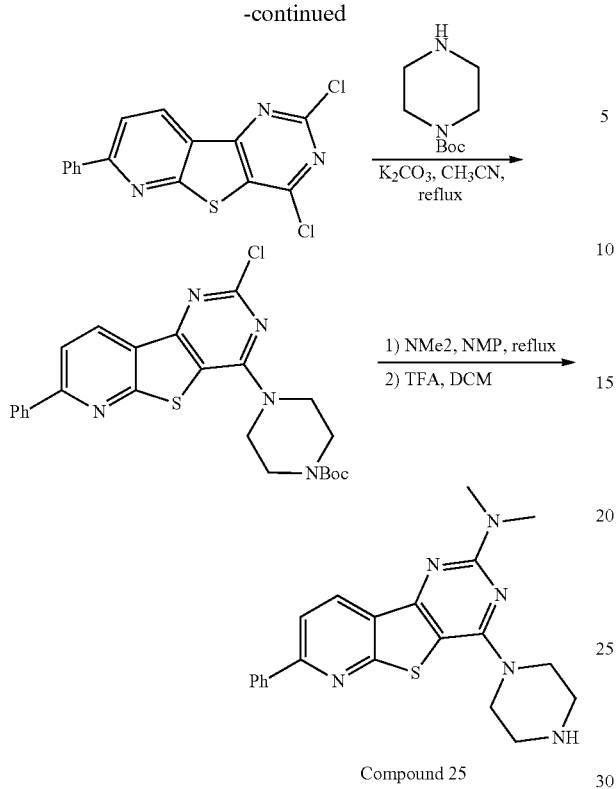
Compound 25
Compounds 24 and 26 in Table 1 were prepared by a similar method as compound 25.
Example 9. Synthesis of Compound 23
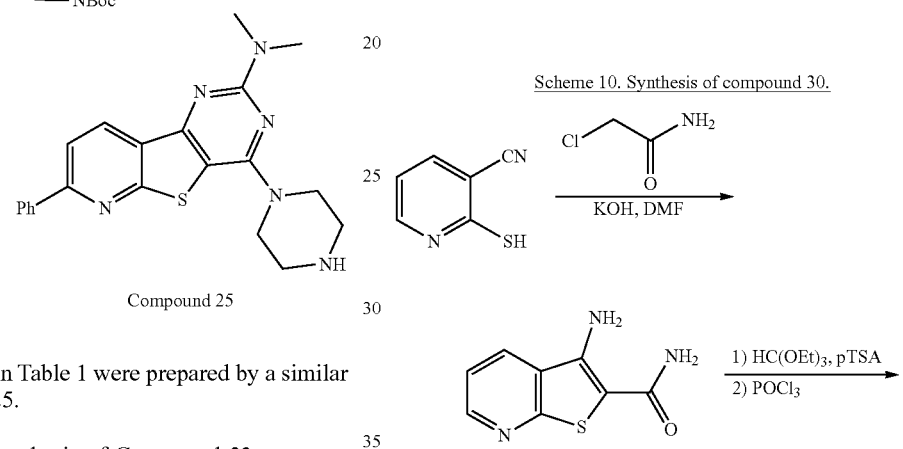
Scheme 9. Synthesis of compound 23.
-continued
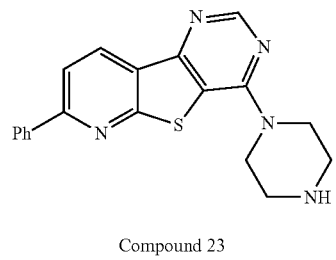
Compound 23
Example 10. Synthesis of Compound 30
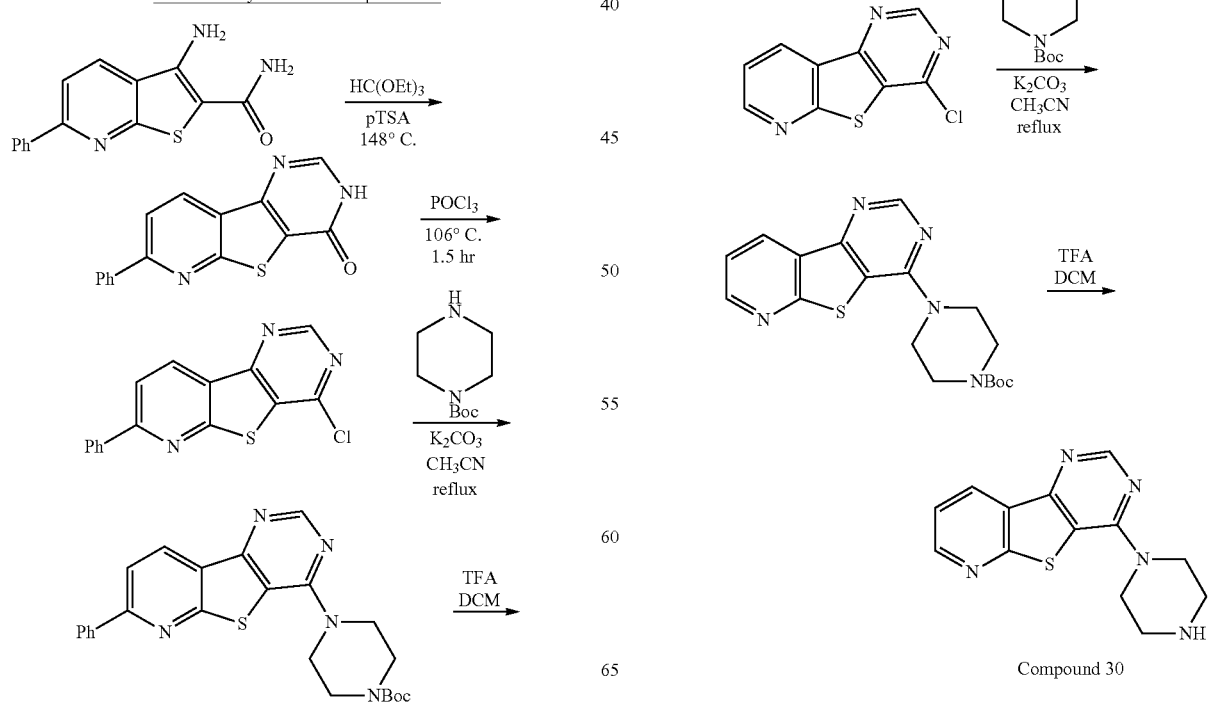
Scheme 10. Synthesis of compound 30.
Compound 30

Example 11. Synthesis of Compound 31

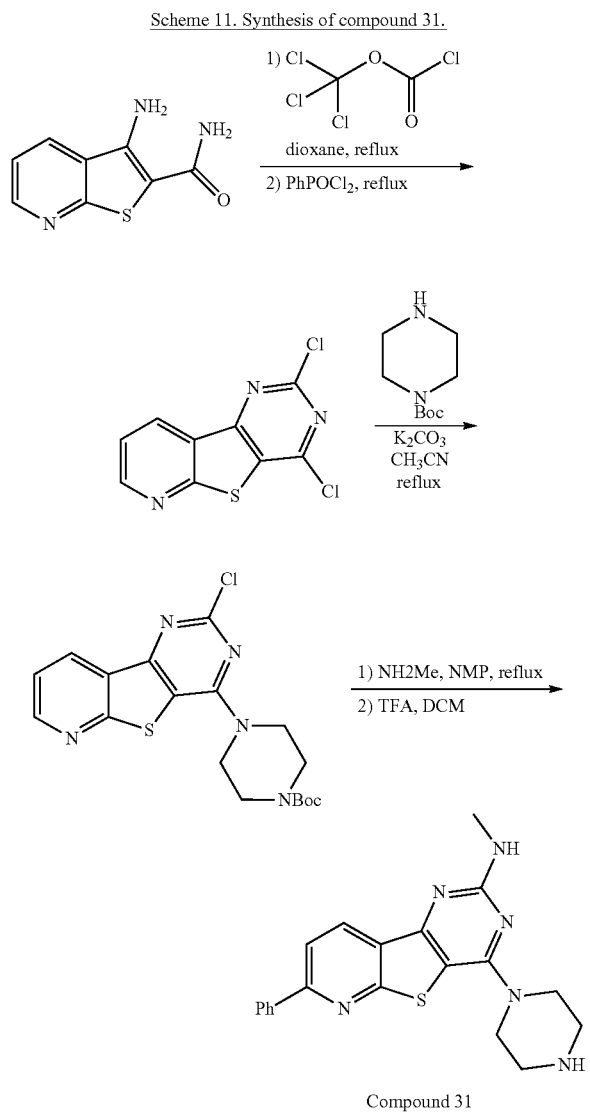

Compound 31

Example 12. In Vitro Binding Assay

To assess GUS inhibition, cleavage of p-nitrophenyl-β-D-glucuronide (PNPG) by purified *E. coli* GUS in the presence of inhibitor was measured. The reaction was performed in 96-well clear-bottom plates at a volume of 50 μL. Each reaction contained 5 μL of 100 nM *E. coli* GUS, 5 μL of inhibitor at various concentrations, 10 μL of 250 mM HEPES and 250 mM NaCl assay buffer, and 30 μL of 1.5 mM PNPG. The reaction was initiated by addition of PNPG and incubated at 37° C. for 2 hours. End point absorbance values at 410 nm were measured using a PHERAstar Plus microplate reader. The resulting data were fit with a four-parameter logistic log function in SigmaPlot 13.0 to determine $IC_{50}$ values. $IC_{50}$ was defined as the concentration of inhibitor that yields a 50% reduction in product formation at equilibrium.

TABLE 1

Data for in vitro potency against *E. coli* (EcGUS), *S. agalactiae* (SaGUS), and *C. perfringens* (CpGUS) β-Glucuronidase.

| Compound No. | EcGUS $IC_{50}$ (nM) | SaGUS $IC_{50}$ (nM) | CpGUS $IC_{50}$ (nM) |
|---|---|---|---|
| 2 | 37600 ± 700 | 22000 ± 7000 | 14300 ± 300 |
| 3 | 5000 ± 500 | 6700 ± 400 | 4500 ± 200 |
| 4 | 30000 ± 10000 | 70000 ± 20000 | 5700 ± 600 |
| 5 | 9000 ± 2000 | 2700 ± 500 | 4500 ± 300 |
| 6 | 2400 ± 400 | 550 ± 70 | 3900 ± 100 |
| 7 | 2400 ± 300 | 550 ± 60 | 4200 ± 300 |
| 8 | 9000 ± 2000 | 5000 ± 1000 | 13700 ± 600 |
| 12 | 130 ± 10 | 63 ± 6 | 120 ± 20 |
| 13 | 500 ± 200 | 180 ± 20 | 350 ± 20 |
| 14 | 800 ± 200 | 320 ± 50 | 480 ± 10 |
| 15 | 130 ± 10 | 62 ± 5 | 180 ± 6 |
| 16 | 70 ± 10 | 39 ± 8 | 180 ± 10 |
| 17 | 190 ± 40 | 90 ± 20 | 290 ± 10 |
| 19 | 170 ± 40 | 640 ± 60 | 220 ± 20 |
| 20 | 130 ± 10 | 690 ± 30 | 53 ± 4 |
| 21 | 100 ± 20 | 340 ± 50 | 100 ± 10 |
| 22 | 150 ± 50 | 700 ± 100 | 230 ± 30 |
| 23 | 130 ± 30 | 550 ± 70 | 440 ± 40 |
| 24 | 180 ± 90 | 480 ± 30 | 450 ± 10 |
| 25 | 190 ± 90 | 270 ± 30 | 160 ± 20 |
| 26 | 120 ± 20 | 490 ± 60 | 410 ± 40 |
| 27 | 80 ± 30 | 1000 ± 200 | 220 ± 20 |
| 28 | 42 ± 6 | 500 ± 200 | 280 ± 50 |
| 29 | 40 ± 8 | 550 ± 70 | 660 ± 90 |
| 30 | 80 ± 20 | 3000 ± 2000 | 577 ± 9 |
| 31 | 36 ± 2 | 2000 ± 1500 | 900 ± 300 |
| 32 | NI | NA | NA |
| 36 | NI | NA | NA |
| 37 | NI | NA | NA |
| 38 | NI | NA | NA |
| 39 | NI | NA | NA |
| 40 | NI | NA | NA |
| 41 | NI | NA | NA |
| 43 | NI | NA | NA |
| 44 | 5400 ± 600 | NA | NA |
| 45 | 140 ± 8 | NA | NA |
| 46 | 1400 ± 40 | NA | NA |
| 47 | 30 ± 3 | NA | NA |
| 48 | 208 ± 3 | NA | NA |
| 49 | 620 ± 50 | NA | NA |
| 50 | 12000 ± 2000 | NA | NA |
| 51 | 900 ± 60 | NA | NA |
| 52 | 6000 ± 100 | NA | NA |

NI = no inhibition; NA = not available; Reference compound Inh9 = $IC_{50}$ of 380 ± 50 (EcGUS); 117 ± 6 (SaGUS); 154 ± 6 (CpGUS).

Figure 3:
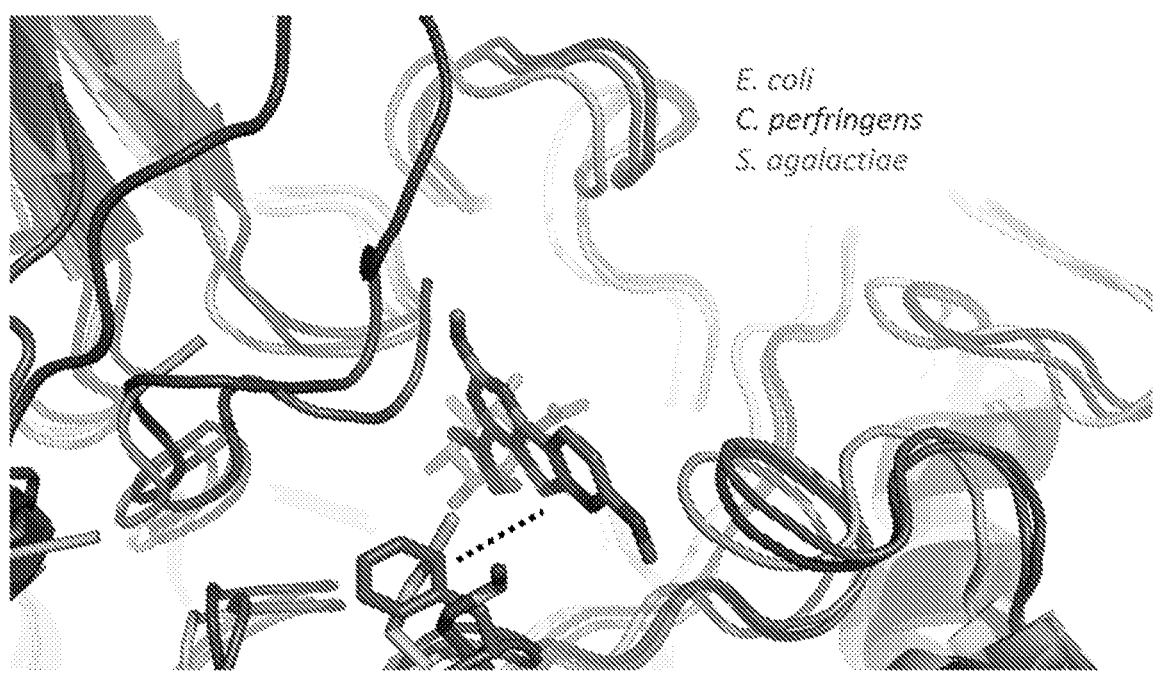
FIG. 3 shows a structural representation of an overlay of the active sites of EcGUS (Blue), CpGUS, and SaGUS with Compound 29.

Surprisingly, it has been observed that removal of the cyclohexyl ring generally reduces potency against SaGUS and CpGUS. This may be seen, for example, in compounds 19-31. Without being bound by theory, it is believed that this is due to structural differences within the loop portion in each GUS ortholog. For example, as shown in FIG. 3, the loops from adjacent monomers form the "back end" of the inhibitor binding site, which, according to structural analysis, is where the cyclohexyl group is present. Without being bound by theory, it is believed that the significant sequence differences between the loops of the different GUS orthologs may account for the potency difference against SaGUS and CpGUS. The respective loop sequences are: EcGUS:

```
EcGUS: NLSLGIG-FEAGNKPKE;

CpGUS: HLNFMATGFGGDAPKRD;

SaGUS: FQNFNAS-LDLSPKDNG.
```

Additionally, it has also been discovered that substituents at the $R_2$ position plays an important role in specific inhibition of one GUS ortholog over another. For example, in compounds 22-26, phenyl substituted analogs may interact more favorably with EcGUS, but show reduced potency against SaGUS and CpGUS. Without being bound by theory, such specific inhibition may be the result of sequence differences in the active site. For example, F448 is a residue within the active site that is unique to EcGUS, and may allow it to interact with a planar aromatic moiety in a way that both SaGUS and CpGUS cannot, since both of these orthologs have a methionine at the same position. Such an interaction may be from a favorable pi-pi stacking interaction.

All technical and scientific terms used herein have the same meaning. Efforts have been made to ensure accuracy with respect to numbers used (e.g. amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound of Formula I:

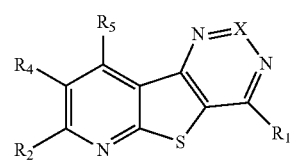

(I)

or a pharmaceutically acceptable salt thereof, wherein, $R_1$ is

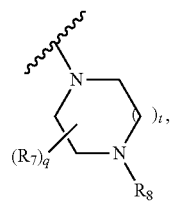

wherein t and q are each 1, $R_7$ is H, and $R_8$ is H;

$R_2$ is $-NR_FR_G$, wherein;

$R_F$ and $R_G$ are independently selected from the group consisting of H, linear or branched $C_{1-6}$ alkyl optionally substituted with halo, amino or hydroxyl, optionally substituted benzyl, and $C_{3-8}$ cycloalkyl;

and $R_4$ and $R_5$ are taken together with the carbon to which each is attached to form an optionally substituted cyclohexyl ring.

2. A compound having the structure

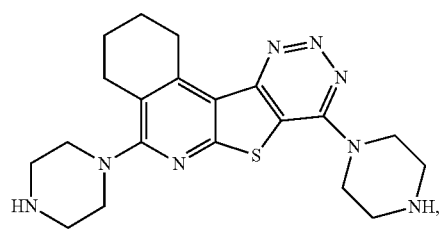 [SMILES: C1CCc2c(c(N3CCNCC3)nc3sc4c(N5CCNCC5)nnnc4c23)C1]

or a pharmaceutically acceptable salt thereof.

3. The compound of claim 1, which is selected from

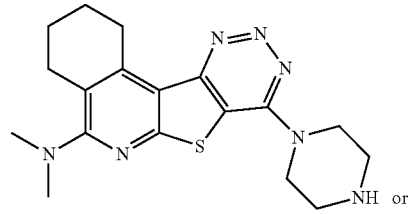

-continued
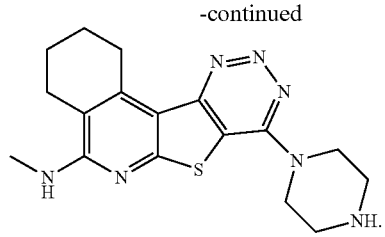
* * * * *